(12) United States Patent
Imai et al.

(10) Patent No.: US 9,002,718 B2
(45) Date of Patent: Apr. 7, 2015

(54) MEDICATION MANAGING APPARATUS

(75) Inventors: Yutaka Imai, Sendai (JP); Tomonori Inoue, Kyoto (JP); Kenji Eda, Suita (JP); Takahide Tanaka, Otsu (JP)

(73) Assignees: Omron Healthcare Company Ltd., Kyoto-shi (JP); Yutaka Imai, Sendai-Shi (JP)

( * ) Notice: Subject to any disclaimer, the term of this patent is extended or adjusted under 35 U.S.C. 154(b) by 2215 days.

(21) Appl. No.: 11/817,217

(22) PCT Filed: Feb. 22, 2006

(86) PCT No.: PCT/JP2006/303161
§ 371 (c)(1),
(2), (4) Date: Aug. 27, 2007

(87) PCT Pub. No.: WO2006/092999
PCT Pub. Date: Sep. 8, 2006

(65) Prior Publication Data
US 2009/0043605 A1 Feb. 12, 2009

(30) Foreign Application Priority Data
Feb. 28, 2005 (JP) ................................ 2005-052405

(51) Int. Cl.
*G06Q 50/00* (2012.01)
*G07F 17/00* (2006.01)
(Continued)

(52) U.S. Cl.
CPC ........... *G07F 17/0092* (2013.01); *A61J 7/0481* (2013.01); *A61J 2007/0418* (2013.01); *A61J 2007/0436* (2013.01); *G06Q 50/22* (2013.01)

(58) Field of Classification Search
USPC ........................................................ 705/2, 3
See application file for complete search history.

(56) References Cited

U.S. PATENT DOCUMENTS 4,660,991 A 4/1987 Simon
5,042,685 A * 8/1991 Moulding et al. ................. 221/1
(Continued)

FOREIGN PATENT DOCUMENTS

EP 0 191 168 8/1986
JP 6-269488 A 9/1994
(Continued)

OTHER PUBLICATIONS

Russian Decision on Grant mailed Jan. 15, 2010, directed at corresponding Russian Application No. 2007135875/14(039227); 17 pages.

(Continued)

*Primary Examiner* — Mark Holcomb
(74) *Attorney, Agent, or Firm* — Morrison & Foerster LLP

(57) ABSTRACT

When the present time of a clock circuit is a medication time recorded in advance in a SD card, a notice that the medication time has come is given by a voice output portion or the like. Presence/absence of a medicine package in each block of a medicine package case is sensed by a medicine package sensor. The time point and the presence/absence of the medicine package are recorded in the SD card. A notice corresponding to the presence/absence is output. At a time except for the medication time, taking-out of the case, opening/closing of the cover, taking-out and return of the medicine package are recorded in the SD card based on detection signals from the medicine package sensor, medicine package case sensor, and case cover opening/closing sensor. A notice corresponding to the sensed situation is output.

13 Claims, 25 Drawing Sheets

(51) Int. Cl.
*A61J 7/04* (2006.01)
*G06Q 50/22* (2012.01)

(56) References Cited

U.S. PATENT DOCUMENTS

| | | | | |
|---|---|---|---|---|
| 5,472,113 | A | * | 12/1995 | Shaw ................................ 221/7 |
| 6,142,375 | A | * | 11/2000 | Belka et al. ................... 235/454 |
| 6,439,422 | B1 | * | 8/2002 | Papp et al. ...................... 221/13 |
| 7,369,919 | B2 | * | 5/2008 | Vonk et al. .................... 700/236 |
| 2004/0167408 | A1 | | 8/2004 | Ashida et al. |
| 2005/0087473 | A1 | * | 4/2005 | Fabricius et al. ............. 206/534 |

FOREIGN PATENT DOCUMENTS

| | | |
|---|---|---|
| JP | 6-511183 A | 12/1994 |
| JP | 8-505305 A | 6/1996 |
| JP | 2002-291840 A | 10/2002 |
| JP | 2002-362652 A | 12/2002 |
| JP | 2003-310715 A | 11/2003 |
| JP | 2004-181137 A | 7/2004 |

OTHER PUBLICATIONS

Extended European Search Report mailed Nov. 5, 2012, directed to European Application No. 06714301.6; 7 pages.

* cited by examiner

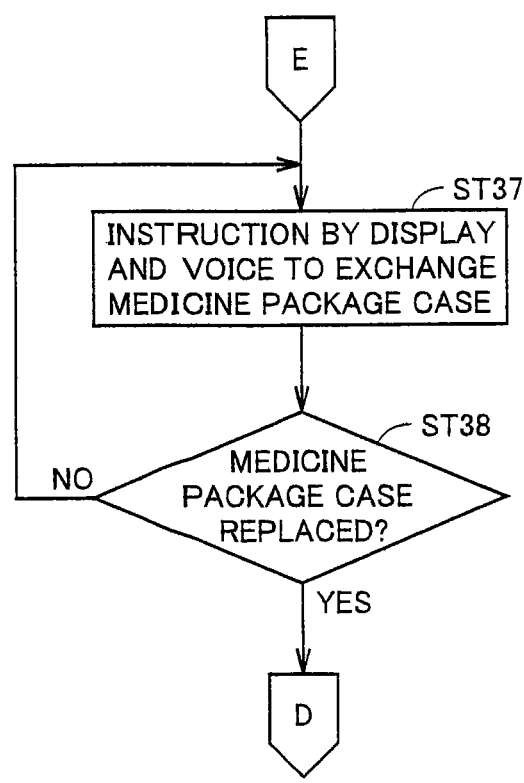

MEDICATION MANAGING APPARATUS

This application is a national stage application under 35 USC 371 of International Application No. PCT/JP2006/303161, filed Feb. 22, 2006, which claims the benefit of Japanese Patent Application No. 2005-052405, filed Feb. 28, 2005, the disclosures of which are hereby incorporated by reference.

TECHNICAL FIELD

The present invention relates to a medication managing apparatus that includes a main body unit that has a medicine package storage portion storing medicine packages containing medicines, that stores/manages medication-related information including a medication instruction time and that gives, when the medication instruction time has come, an instruction/notice of medication.

BACKGROUND ART

Conventionally, there has been an apparatus that includes a medicine storing portion having a plurality of compartments (blocks) for storing medicines to be taken and that gives by voice or display, when the medication time has come, a notice that the medication time has come.

As a medication managing apparatus of this type, to realize automatic recording and displaying of a medication record, there has been proposed a medication managing apparatus including: medicine storage means for storing one or a plurality of medicine(s) of a single dose for a user in divided portions; medication storage means for storing instruction of medication externally entered; medication instruction means for instructing the medicine to be taken from the divided portions stored in the medicine storage means on the basis of the medication instruction of the medication instruction storage means; medication sensing means for sensing taking-out of the medicine instructed by the medication instruction means; storage output means for storing the medicine taking-out record sensed by the medication sensing means, and outputting it externally; and display means for displaying the medicine taking-out record stored in the storage means (see, for example, Japanese Patent Laying-Open No. 2004-181137 (Patent Document 1)).

There has also been disclosed a medicine container having a plurality of medicine chambers, and light sensors respectively corresponding to the chambers for sensing the existence/absence of the medicine. When the medicine is taken out from a medicine chamber, in response to a sensing signal of the light sensor corresponding to the medicine chamber an identification signal of the light sensor and the detection time thereof are stored in memory. The time data stored in the memory is output externally based on an instruction from an external apparatus (see, for example, Japanese Patent Laying-Open No. 2002-362652 (Patent Document 2)).

Patent Document 1: Japanese Patent Laying-Open No. 2004-181137
Patent Document 2: Japanese Patent Laying-Open No. 2002-362652

DISCLOSURE OF THE INVENTION

Problems to be Solved by the Invention

A medication managing apparatus gives to a user a notice of medication time when the medication time has come. The user would not miss a dose, or would not take double doses, and therefore greatly benefits from the apparatus. However, simply storing the medication time in advance and giving a notice of medication time when the medication time has come are not actually enough to avoid missing a dose or taking double doses. On the other hand, in the case where a doctor administers medicines to a patient by a medication managing apparatus, it is desirable that such data is obtained that enables the doctor to precisely determine whether the patient's symptom after taking the medicines for a certain period is attributed to continuously missed doses, double doses, inappropriate medicines, or a change in the condition of the patient's disease. According to Patent Document 1, medication data at a medication time is only stored, and other situation cannot be known. According to Patent Document 2, a medication time is stored, but the medication states at the medication notice time and at the other times cannot be stored in detail.

The present invention is therefore made in view of the foregoing problems, and an object of the present invention is to provide a medication managing apparatus with which a medication condition can be recorded at both of a medication notice time and other times.

Means for Solving the Problems

A medication managing apparatus according to the present invention includes: a medicine package storage portion having a plurality of blocks each storing a medicine package containing a single dose of medicine for a user; storing means for storing in advance a plurality of medication times; medication time noticing means for giving a notice, every time the medication time has come, that the medication time has come; a medicine package sensor provided for each block of the medicine package storage portion to sense presence/absence of the medicine package in the block; first processing means for, when the medication time has come, determining by the medicine package sensor presence/absence of the medicine package in a prescribed block, causing the storing means to store a time point of the determination and the presence/absence of the medicine package, and outputting an instruction for the user in accordance with a detection result; and second processing means for, when taking-out of the medicine package is sensed by the medicine package sensor at a time except for the medication time, causing the storing means to store a time point of the sensing and the taking-out, and outputting a desired instruction to the user.

In the medication managing apparatus of the present invention, desirably, the storing means is a storage medium externally attached to a main body, and the medication managing apparatus comprises a storage medium attachment portion for attaching the storage medium. Desirably, a commercially available storing media is employed in light of the availability and costs. On the other hand, if a patient make any changes to the storage medium without permission, the management cannot be achieved. Accordingly, desirably a pair of secret numbers for the storage medium and the medication management apparatus is stored in advance so that other medium cannot be used.

In the medication managing apparatus of the present invention, the first processing means can give a notice, if number of the medicine package being taken out sensed by the medicine package sensor is plural when the medication time has come, to return an excessive medicine package.

In the medication managing apparatus of the present invention, after giving the notice to return the excessive medicine package, the first processing means can determine whether or not the medicine package is returned based on an output of the medicine package sensor, and if the medicine package is not returned, the first processing means can store in the storing means taking-out of a plurality of medicine packages together with a time point.

In the medication managing apparatus of the present invention, the first processing means can determine whether or not the medicine package is returned, and if all the medicine packages are returned, the first processing means can give a notice of medication instruction.

In the medication managing apparatus of the present invention, the first processing means can determine whether or not the medicine package is returned, and if all but one medicine packages are returned, the first processing means can store in the storing means taking-out of one medicine packages together with a time point.

In the medication managing apparatus of the present invention, the medicine package storage portion can be constituted of a medicine package case removably attached to the main body, wherein the medication managing apparatus includes a medicine package case sensor sensing attachment and removal of the medicine package case to and from the main body, and wherein the second processing means can give an instruction/notice to set the medicine package case if taking-out of the medicine package case is sensed at a time except for the medication time.

In the medication managing apparatus of the present invention, the second processing means can determine whether or not the medicine package case is set, detect whether there is a change in number of the medicine packages when the medicine package case is set, and give a notice to return a medicine package excessively taken out if the number of the medicine packages decreases.

In the medication managing apparatus of the present invention, the second processing means can determine whether or not the medicine package case is set, detect whether there is a change in number of the medicine packages when the medicine package case is set, and give an instruction/notice to take out the medicine package with designation of location of the medicine package if the number of the medicine packages increases.

In the medication managing apparatus of the present invention, the second processing means can determine whether or not the medicine package is returned based on an output of the medicine package sensor, and if it is not returned, the second processing means can store in the storing means taking-out of the medicine package together with a time point.

On the other hand, the medication managing apparatus of the present invention may be so configured that the main body and the medicine package case are irremovably and integrally formed. In this case, while it is inconvenient to replace the medicine packages or to carry, it may be realized at low costs.

In the medication managing apparatus of the present invention, the medicine package storage portion is provided with an openable/closable cover covering the entire blocks, wherein the medication managing apparatus includes a cover opening/closing sensor sensing opening/closing of the cover, and wherein the second processing means can give an instruction/notice to close the cover when the cover is opened at a time except for the medication time.

In the medication managing apparatus of the present invention, the second processing means can determine whether or not the cover is closed, detects whether there is a change in number of the medicine packages when the cover is closed, and gives a notice to return a medicine package excessively taken out if the number of the medicine packages decreases. In the medication managing apparatus of the present invention, the second processing means can determine whether or not the cover is closed, detects whether there is a change in number of the medicine packages when the cover is closed, and can give an instruction/notice to take out the medicine package with designation of location of the medicine package if the number of the medicine packages increases.

In the medication managing apparatus of the present invention, the medicine package storage portion is constituted of a medicine package case removably attached to a main body, and the medication managing apparatus can give an instruction/notice to add a medicine package or replace the medicine package case with a new medicine package case if remaining quantity of the medicine package in the medicine package case reaches zero.

Effects of the Invention

According to the present invention, that a medicine is taken out is recorded in the case where the stored medication time has come and in the case of the other times. In each case, various changes other than the taking-out are stored. Therefore, detailed medication management can be achieved, and detailed data as to medication can be sold.

BRIEF DESCRIPTION OF THE DRAWINGS

FIG. 30 is a flowchart illustrating the management processing operation of the medication managing apparatus, together with FIG. 27, FIG. 28 and FIG. 29.

Figure 1:
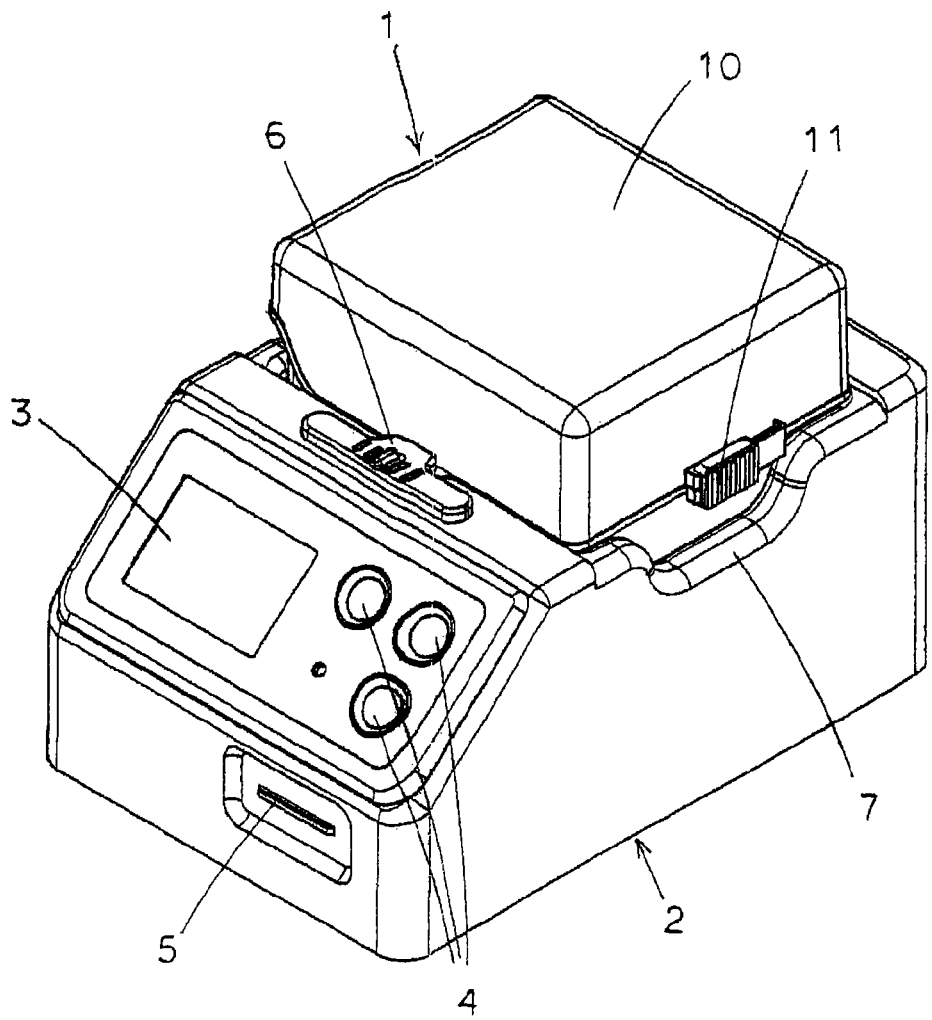
FIG. 1 is an external perspective view of a medication managing apparatus in accordance with an embodiment.
Figure 2:
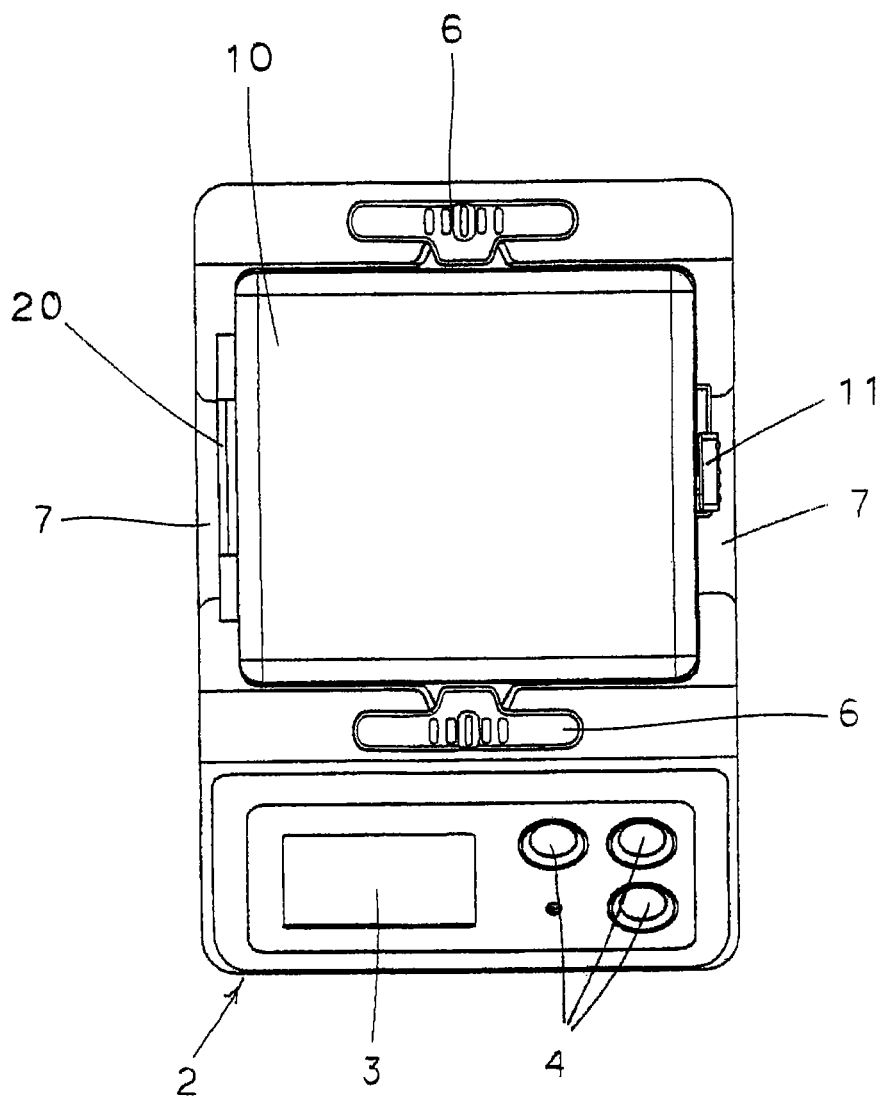
FIG. 2 is a plan view (top view) of the medication managing apparatus.
Figure 3:
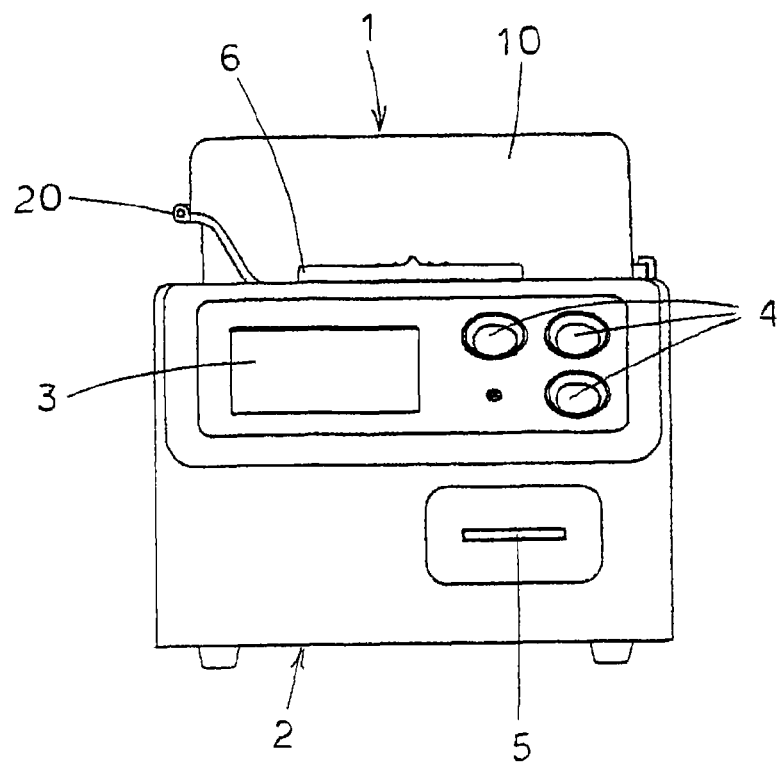
FIG. 3 is a front view of the medication managing apparatus.
Figure 4:
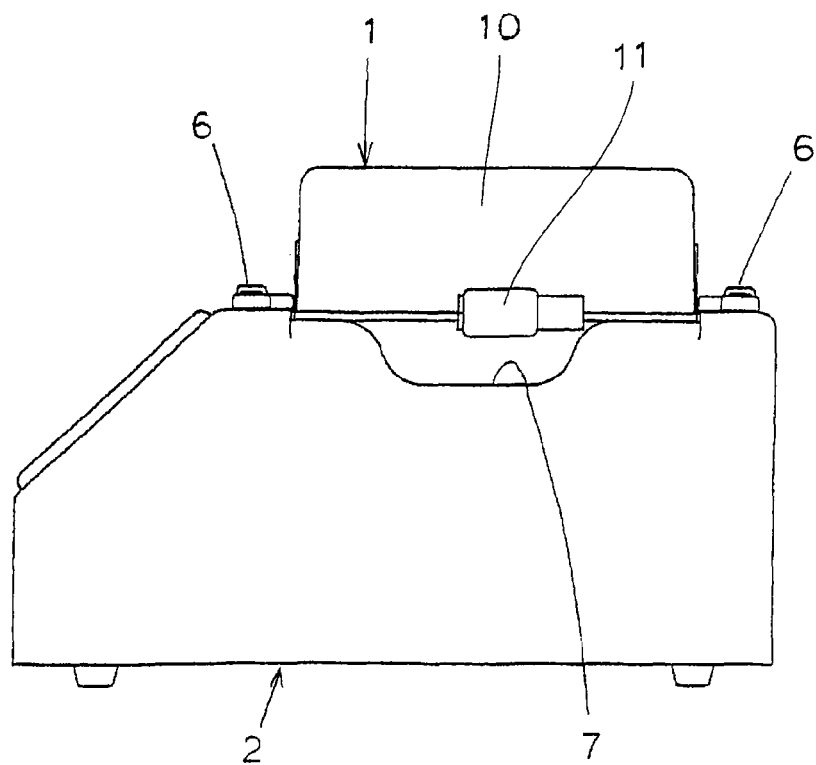
FIG. 4 is a right-side view of the medication managing apparatus.
Figure 5:
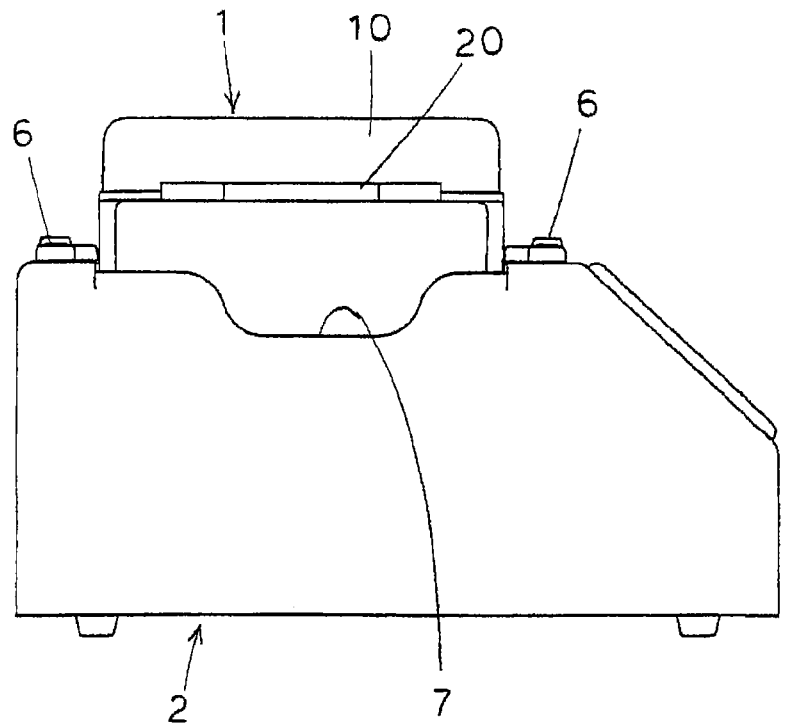
FIG. 5 is a left-side view of the medication managing apparatus.
Figure 6:
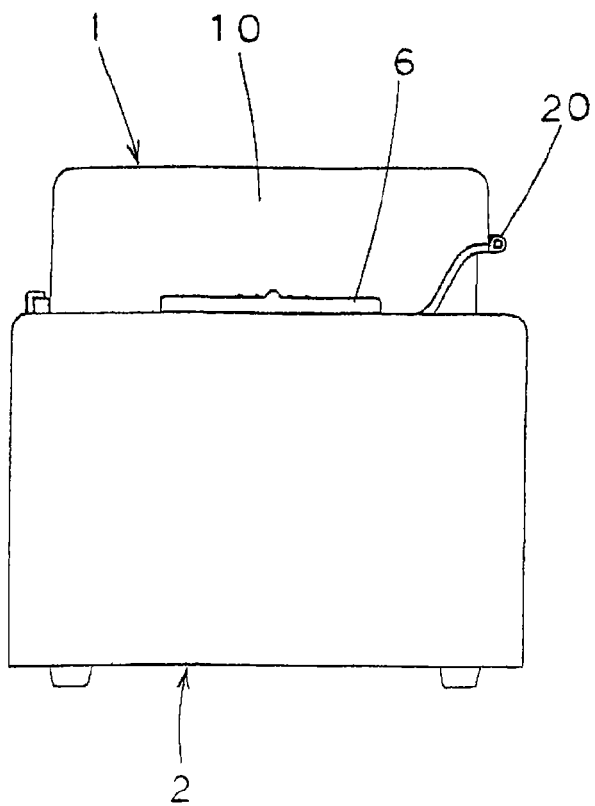
FIG. 6 is a rear view of the medication managing apparatus.
Figure 7:
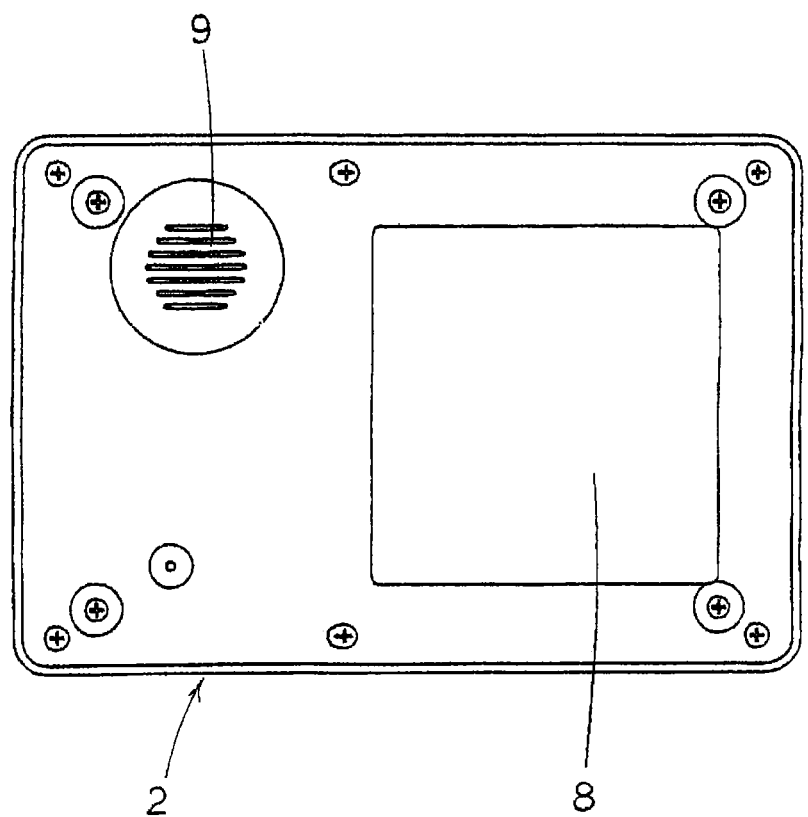
FIG. 7 is a bottom view of the medication managing apparatus.

DESCRIPTION OF THE REFERENCE SIGNS 1 medicine package case, 2 main body unit, 5 slot (storage medium attachment portion), 9 speaker (notice means), 10 cover, 12(a-g) block, 13 wall, 15 opening, 16 support piece, 17 notch portion, 30 storage portion, 35 switch lever (medicine package case sensor), 36 micro-switch (medicine package case sensor), 45, 112 SD card (storage medium), 51-57 medicine package, T1-T9 projection portion, S1-S7 sensor portion (medicine package sensor), L1-L7 light-emitting diode, D1-D7 photodiode, 101 CPU, 102 operation input portion, 103 setting recording portion, 104 display portion, 105 voice output portion, 106 clock portion, 107 recording medium attachment portion, 108 medicine package case sense portion, 109 case cover opening/closing sense portion, 110 medicine package sense portion, 111 power supply portion.

BEST MODES FOR CARRYING OUT THE INVENTION

In the following, the present invention will be described based on an embodiment.

FIG. 1, FIG. 2, FIG. 3, FIG. 4, FIG. 5, FIG. 6, and FIG. 7 respectively show an external perspective view, a plan view (top view), a front view, a right-side view, a left-side view, a rear view and a bottom view of a medication managing apparatus in accordance with the embodiment.

The medication managing apparatus includes a medicine package case (medicine package storage portion) 1 and a main body unit 2 removably storing medicine package case 1 and managing medication-related information including a medication instruction time to give an instruction/notice of medication when the medication instruction time comes. It is noted that the medication managing apparatus in the present embodiment may be so configured that medicine package case 1 is fixedly integrated with main body unit 2.

Medicine package case 1 includes an openable/closable cover 10 and a slide knob 11 for fixing/releasing the closed state of cover 10.

Main body unit 2 includes a display portion (LCD) 3 displaying information such as time, medication instruction time, and medication history, a button 4 for turning on/off the power, setting the time and switching display, and a slot (storage medium attachment portion) 5 for attaching, for example, an SD card 45 (storage medium, see FIG. 23) as information storing means for storing medication-related information including the medication instruction time.

Provided on the top of main body unit 2 is a pair of slide knobs 6 for fixing/releasing the storage state of medicine package case 1 in main body unit 2. In a click position of slide knob 6, medicine package case 1 is fixed so that it is not easily detached from main body unit 2. In addition, a pair of notch portions 7 are formed on the top of main body unit 2 to facilitate removal of medicine package case 1 from main body unit 2.

On the other hand, a battery cover 8 is removably mounted on the bottom of main body unit 2, so that a battery as a power supply can easily be put in/taken out by removing battery cover 8. Here, AC may be used alone or in combination as a power supply. In this case, an insertion slot having an AC code connected thereto is provided at an appropriate place of main body unit 2. In addition, a speaker 9 is provided as notice means for giving a notice of medication instruction time when the medication instruction time has come.

Figure 8:
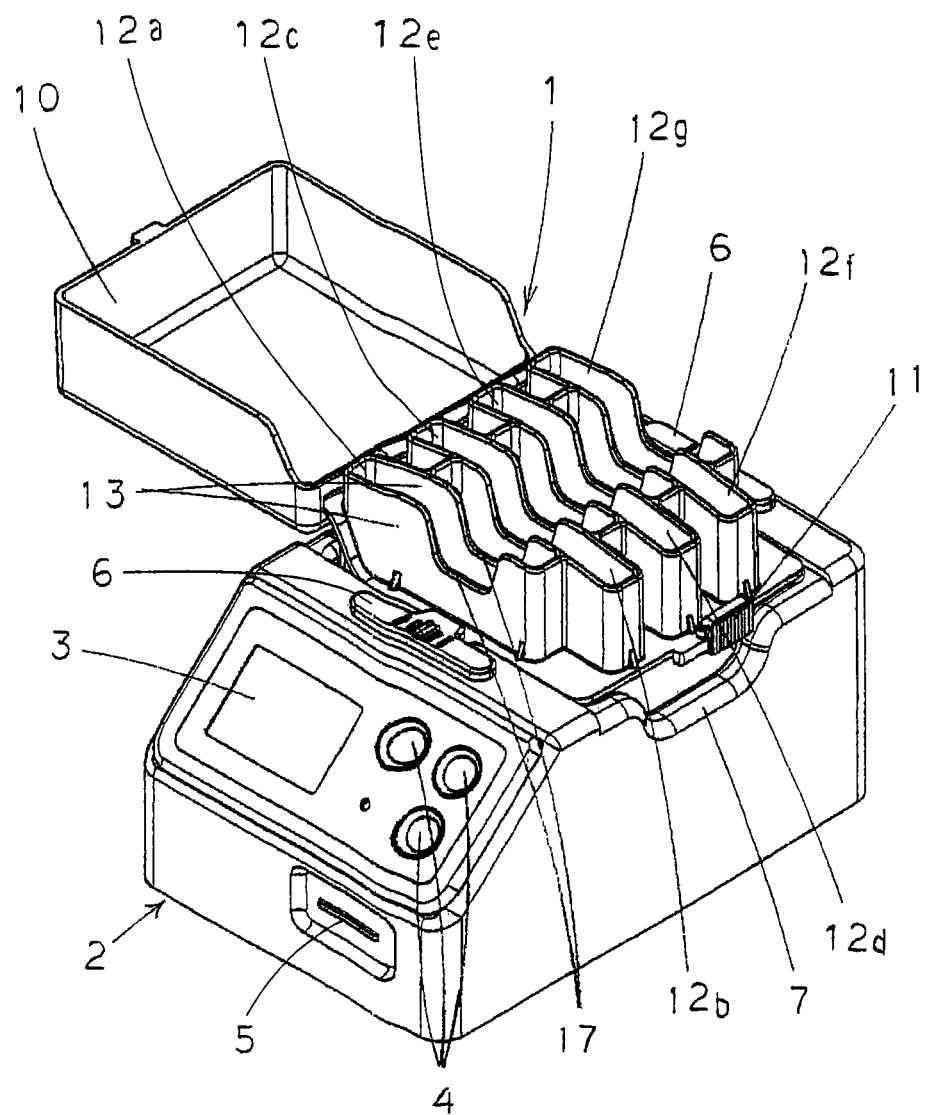
FIG. 8 is an external perspective view in which a cover of a medicine package case of the medication managing apparatus is opened.
Figure 9:
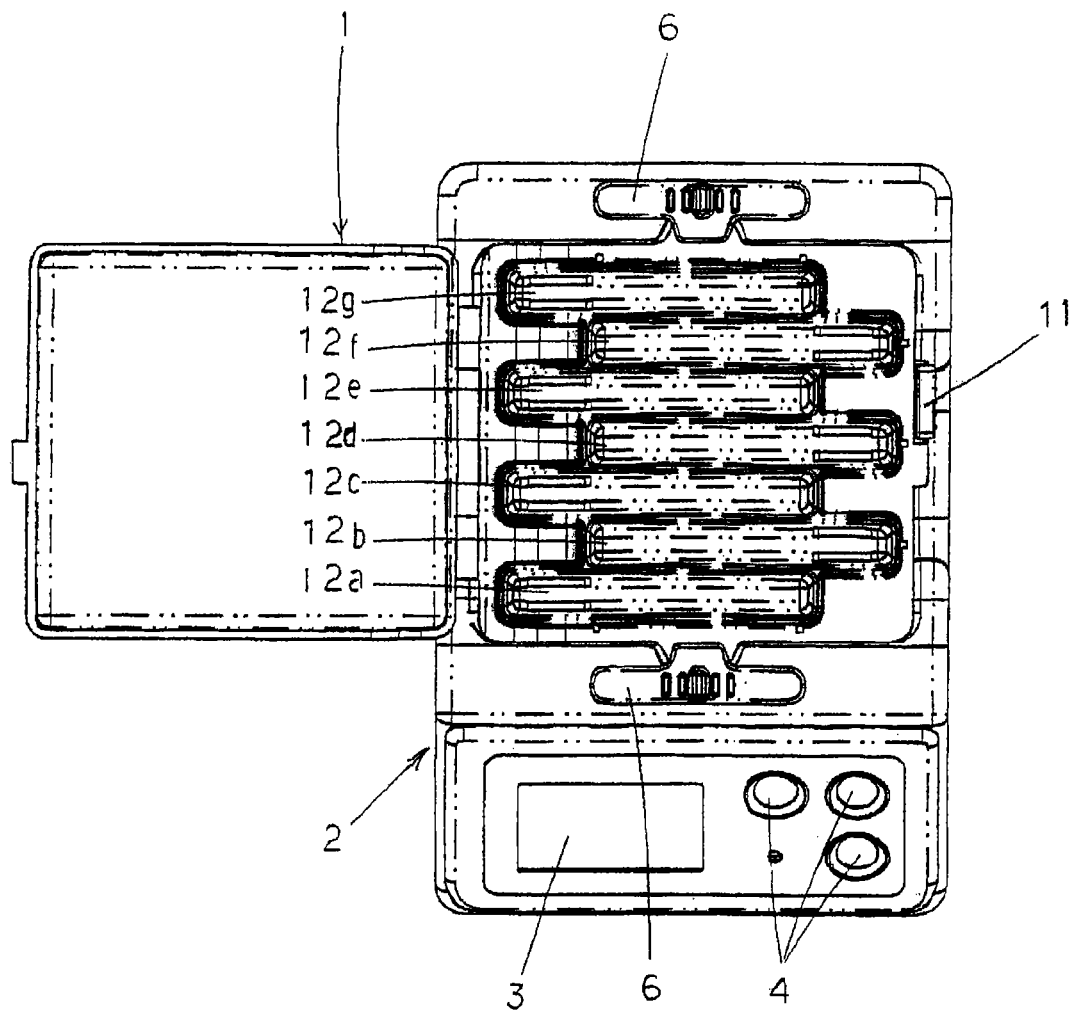
FIG. 9 is a plan view (top view) in which the cover of the medicine package case of the medication managing apparatus is opened.
Figure 10:
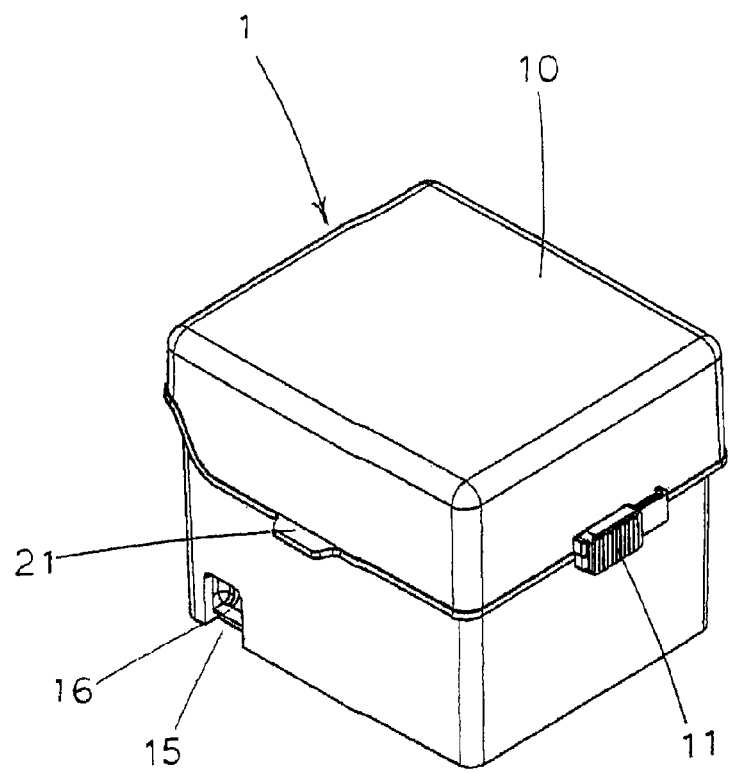
FIG. 10 is an external perspective view of the medicine package case in the medication managing apparatus as viewed from the front side.
Figure 11:
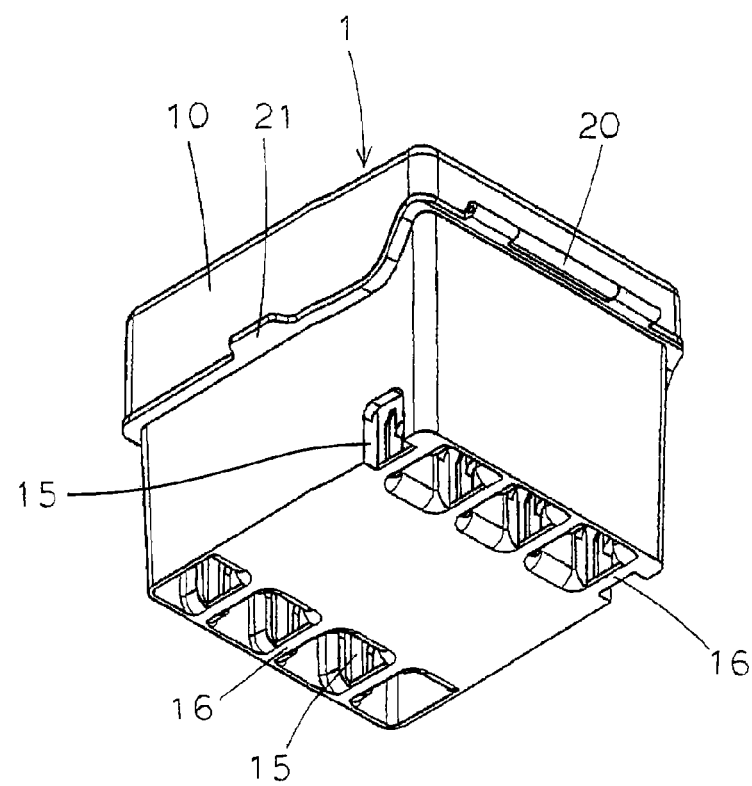
FIG. 11 is an external perspective view of the medicine package case in the medication managing apparatus as viewed from the back side.
Figure 12A:
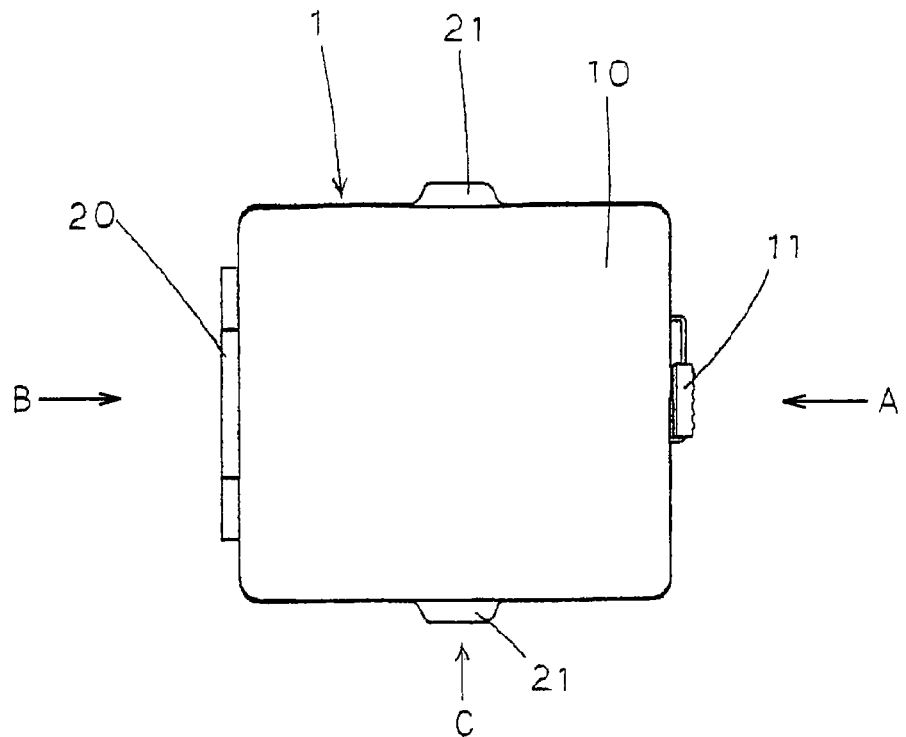
FIG. 12A is a plan view (top view) of the medicine package case in the medication managing apparatus.
Figure 12B:
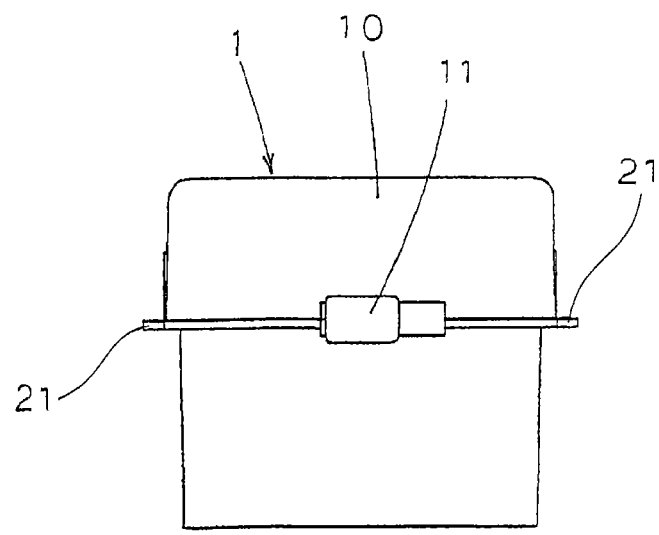
FIG. 12B is a view (front view) of the medicine package case in the medication managing apparatus as viewed from arrow A in FIG. 12A.
Figure 13A:
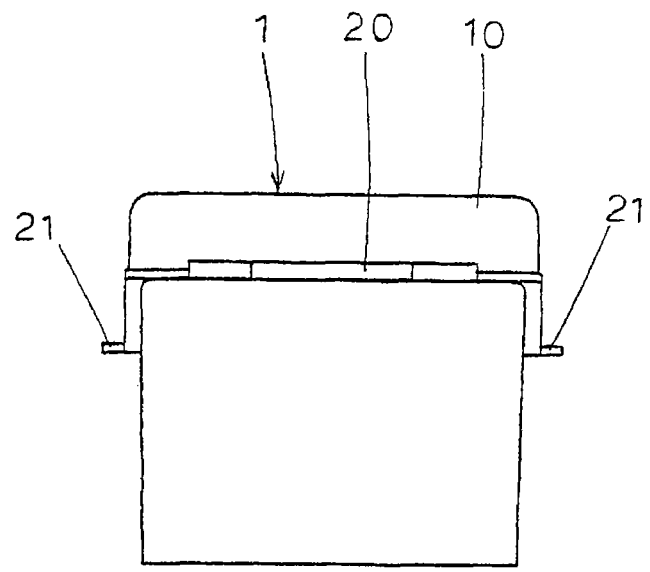
FIG. 13A is a view (rear view) of the medicine package case in the medication managing apparatus as viewed from arrow B in FIG. 12A.
Figure 13B:
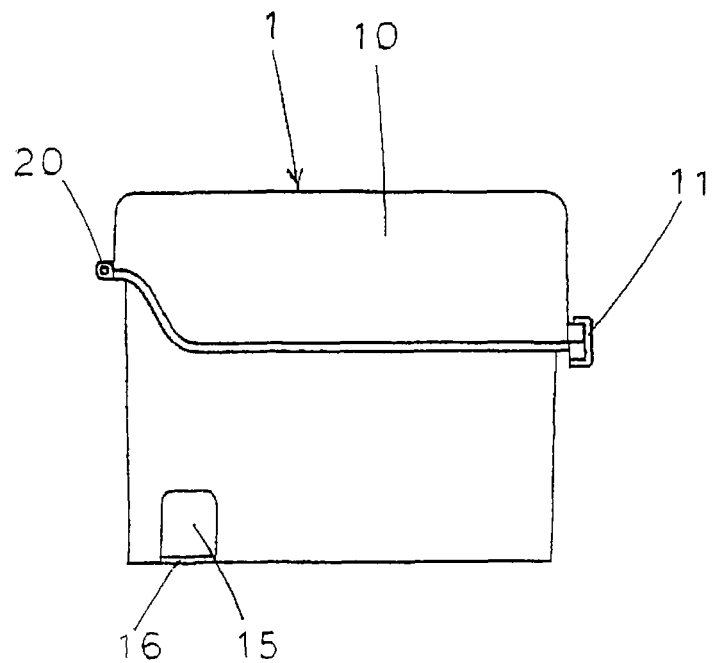
FIG. 13B is a view (left-side view) of the medicine package case in the medication managing apparatus as viewed from arrow C in FIG. 12A.
Figure 14:
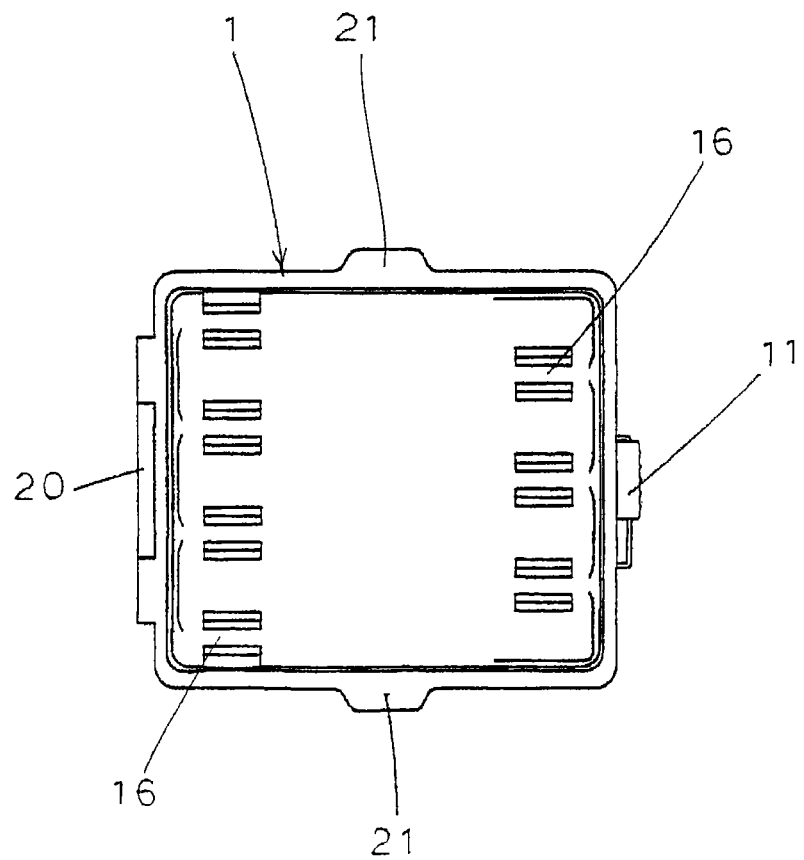
FIG. 14 is a bottom view of the medicine package case in the medication managing apparatus.
Figure 15:
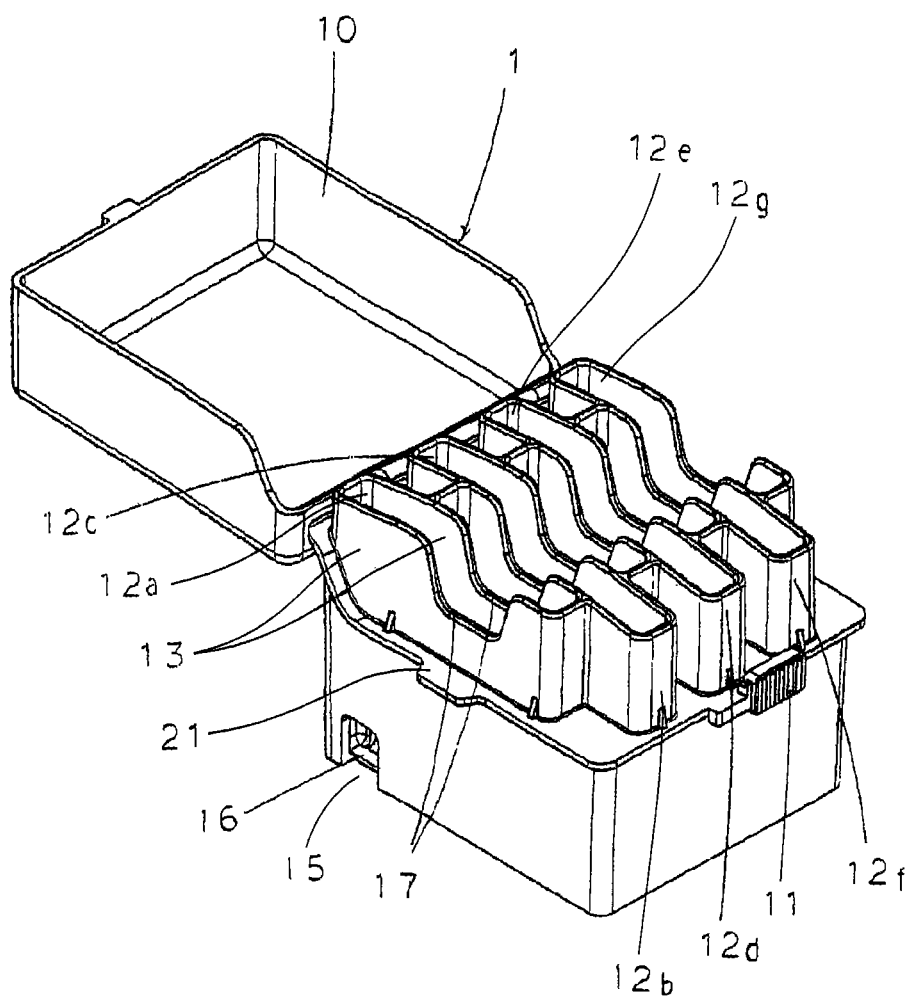
FIG. 15 is an external perspective view in which the cover of the medicine package case is opened in the medication managing apparatus.
Figure 16:
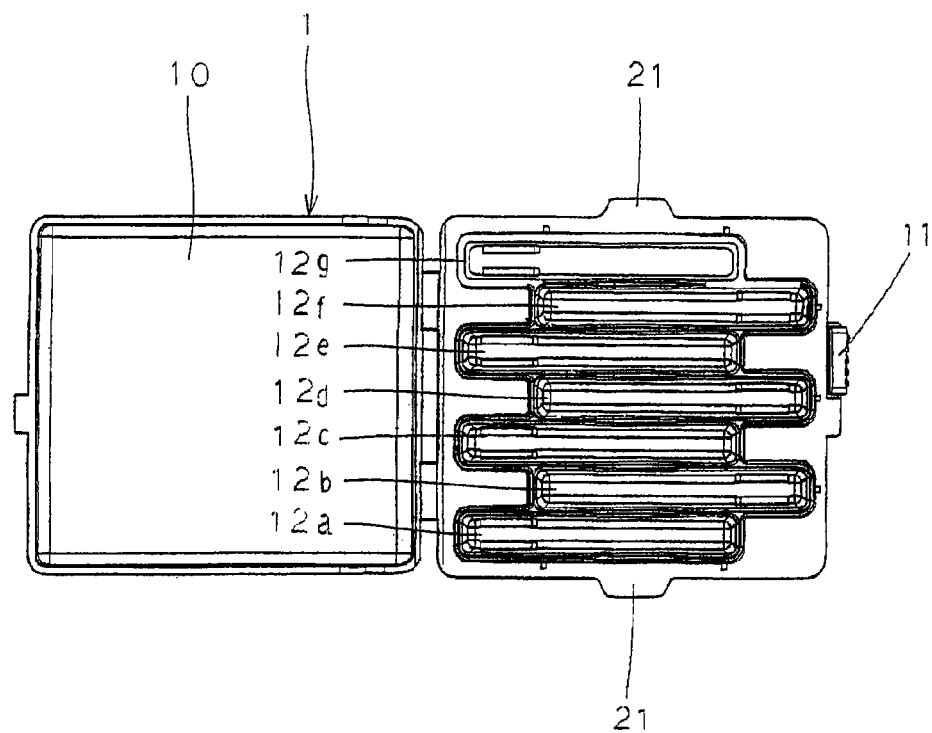
FIG. 16 is a plan view (top view) in which the cover of the medicine package case is opened in the medication managing apparatus.
Figure 17:
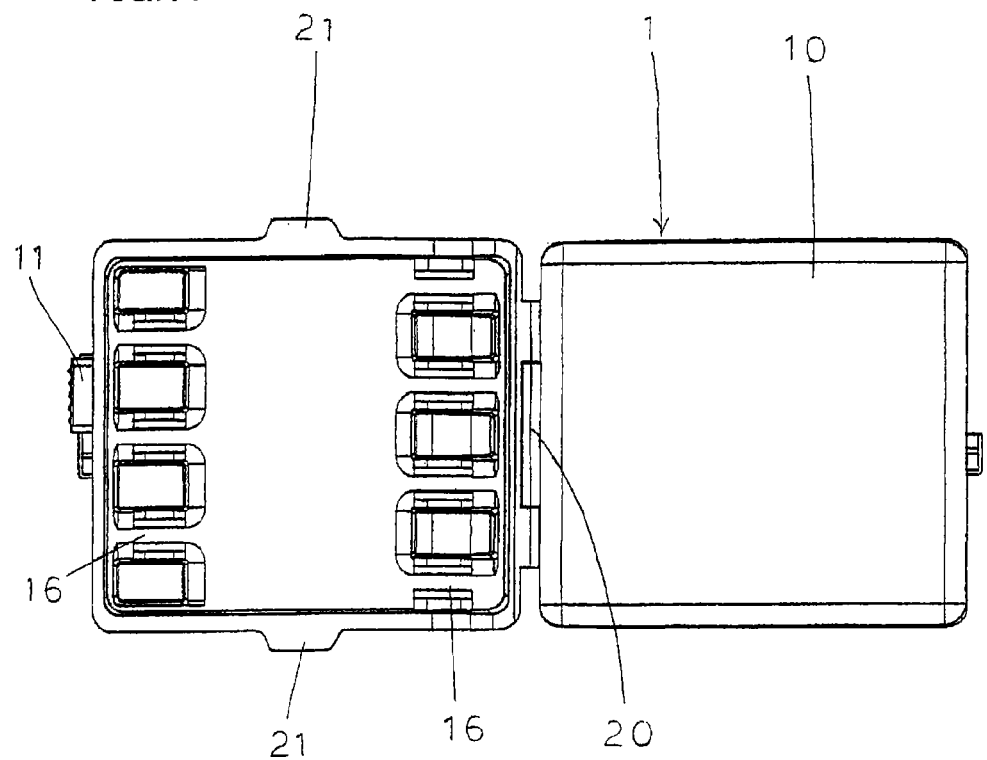
FIG. 17 is a bottom view in which the cover of the medicine package case is opened in the medication managing apparatus.

In this medication managing apparatus, FIG. 8 and FIG. 9 respectively show an external perspective view and a plan view (top view) in which cover 10 of medicine package case 1 is opened. FIG. 10 and FIG. 11 respectively show an external perspective view of medicine package case 1 as viewed from the front side and the back side. FIG. 12A shows a plan view (top view), FIG. 12B shows a view (front view) as viewed from arrow A in FIG. 12A, FIG. 13A shows a view (rear view) as viewed from arrow B in FIG. 12A, FIG. 13B shows a view (left-side view) as viewed from arrow C in FIG. 12A, and FIG. 14 shows a bottom view of medicine package case 1. FIG. 15, FIG. 16 and FIG. 17 respectively show an external perspective view, a plan view (top view) and a bottom view in which cover 10 is opened.

Medicine package case 1 has cover 10 coupled thereto with a shaft portion 20 in an openable/closable manner and has a plurality (here, seven) of blocks 12(a-g) each storing a medicine package (not shown) containing a medicine to be taken by a user. As is clear from the drawings, blocks 12(a-g) are provided in parallel with each other in the depth direction, each positioned orthogonally to the depth direction of main body unit 2, and are arranged to be alternately displaced in the orthogonal direction. Blocks 12(a-g) are each divided by a pair of opposing walls (FIG. 8, FIG. 15) 13, and wall 13 which divides the adjacent blocks is shared by these blocks.

At the lower portion of each wall 13 forming each block 12(a-g), openings 15 are formed to face each other such that a medicine package stored in each block is sandwiched therebetween. Opening 15 reaches a support piece 16 provided on the bottom of each block 12(a-g). Here, support piece 16 is continuous on the bottom face of medicine package case 1. In addition, on the top of each wall 13 forming each block 12(a-g), a notch portion 17 is formed extending downwardly from the upper edge thereof. Notch portion 17 facilitates removal of a medicine package from each block 12(a-g).

Furthermore, medicine package case 1 is provided with a pair of flanges 21 protruding from an outer wall thereof. These flanges 21 are positioned in a pair of flange reception portions 32 (FIG. 18-FIG. 20) provided on the top of main body unit 2 when medicine package case 1 is stored in main body unit 2. Moving slide knob 6 to the click position with flange 21 fit in flange reception portion 32 prevents flange 21 from being pulled off from flange reception portion 32 thereby to fix the storage state of medicine package case 1 in main body unit 2.

Figure 18:
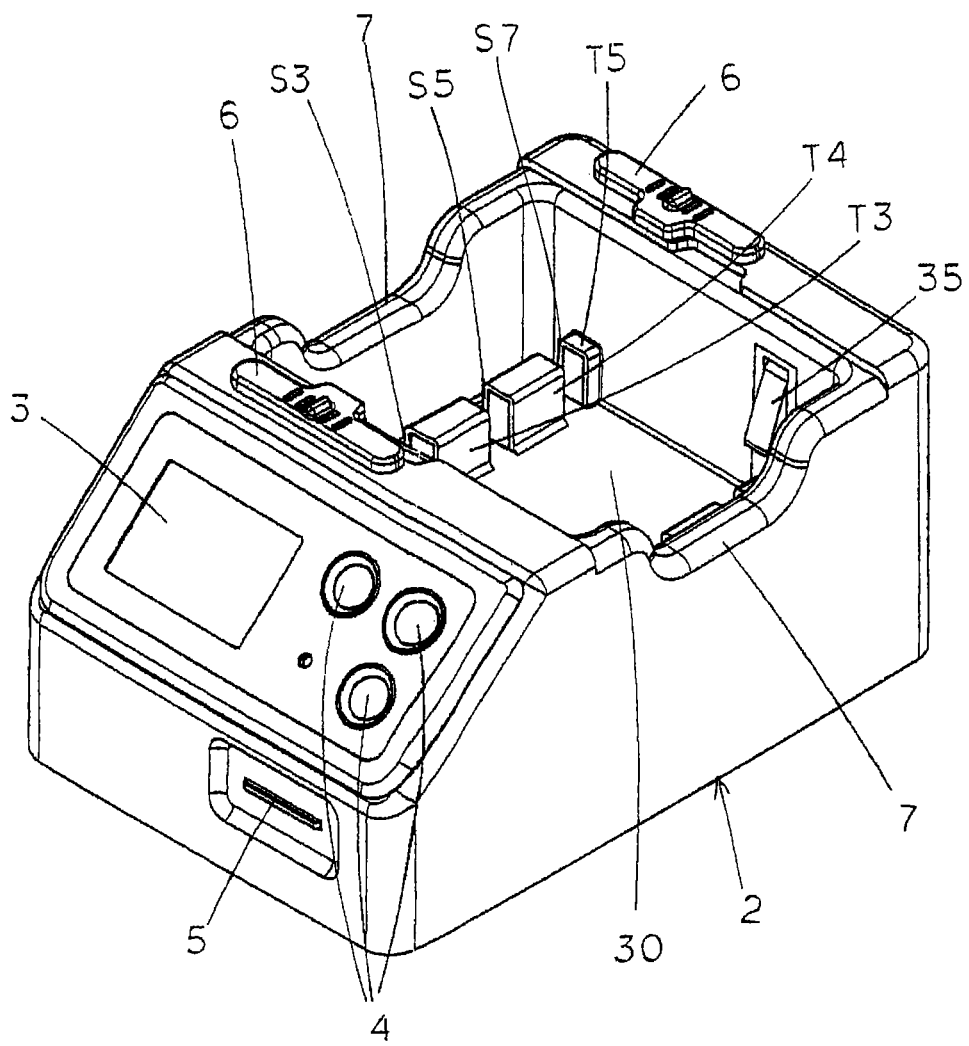
FIG. 18 is an external perspective view of a main body unit in the medication managing apparatus.
Figure 19:
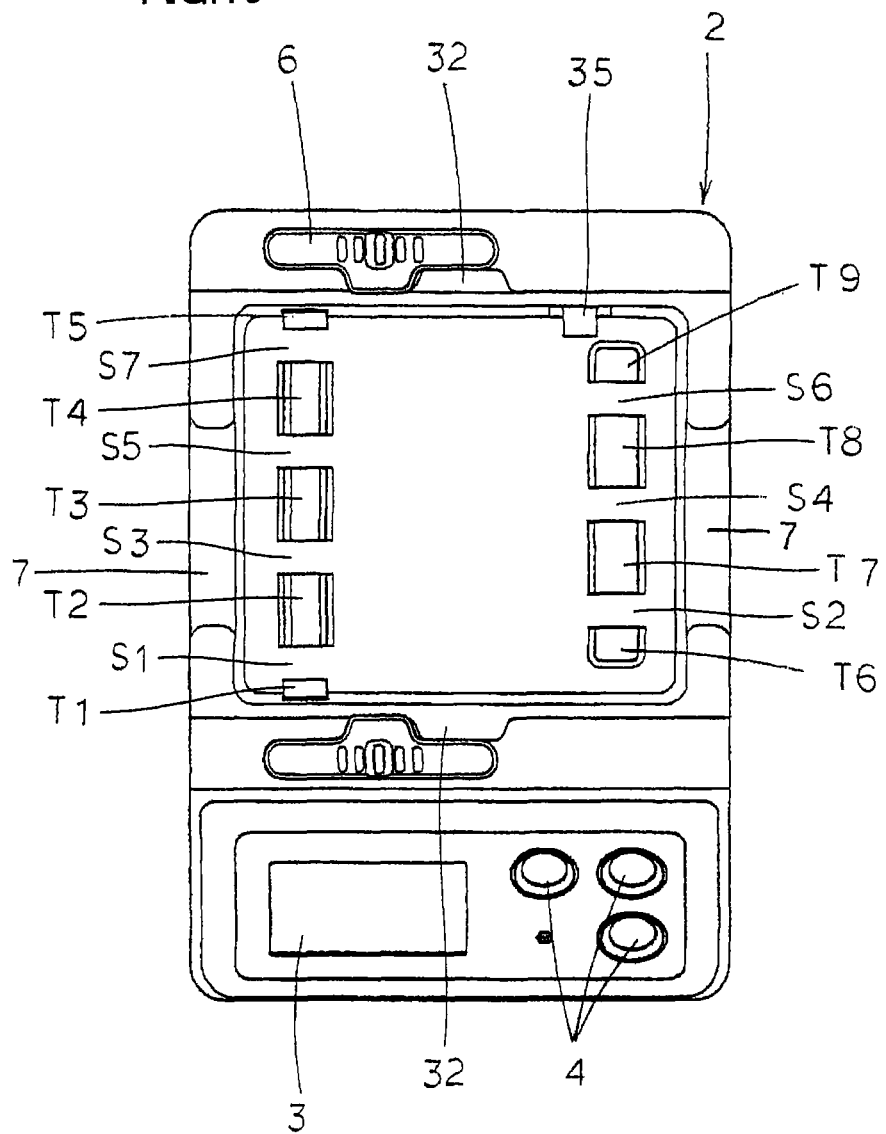
FIG. 19 is a plan view (top view) of the main body unit in the medication managing apparatus.
Figure 20:
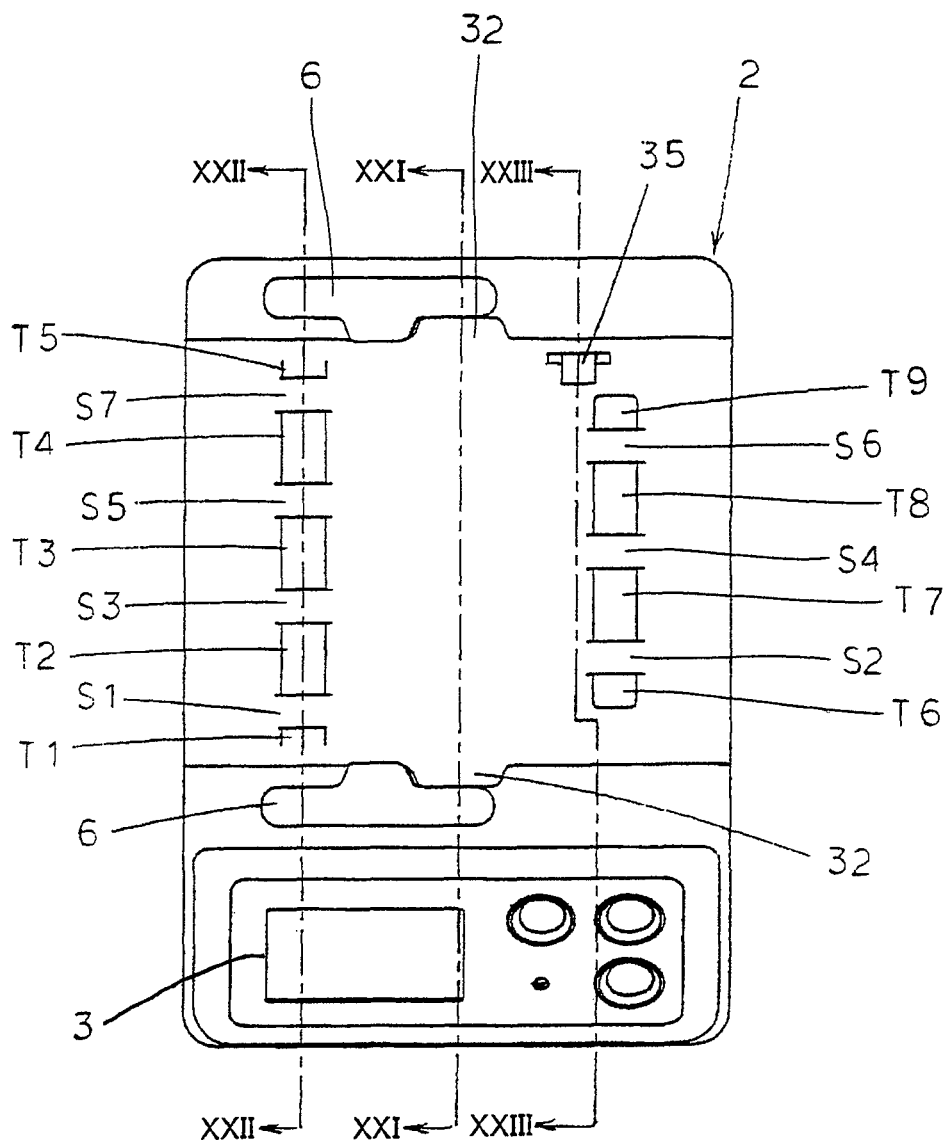
FIG. 20 is a plan view (top view) (a simplified view of FIG. 19) of the main body unit in the medication managing apparatus.
Figure 21:
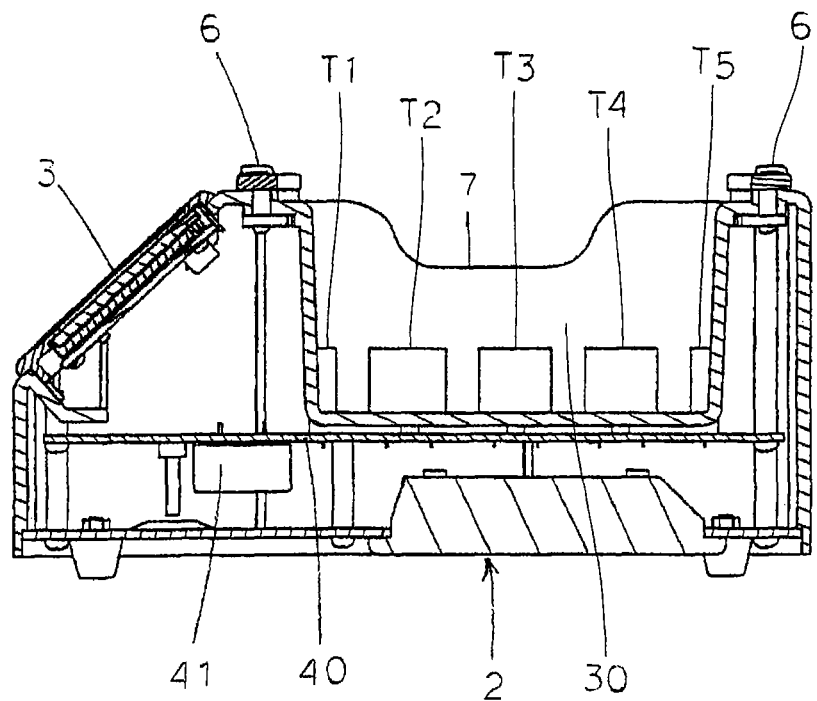
FIG. 21 is a cross-sectional view of the main body unit taken along line XXI-XXI in FIG. 20.
Figure 22:
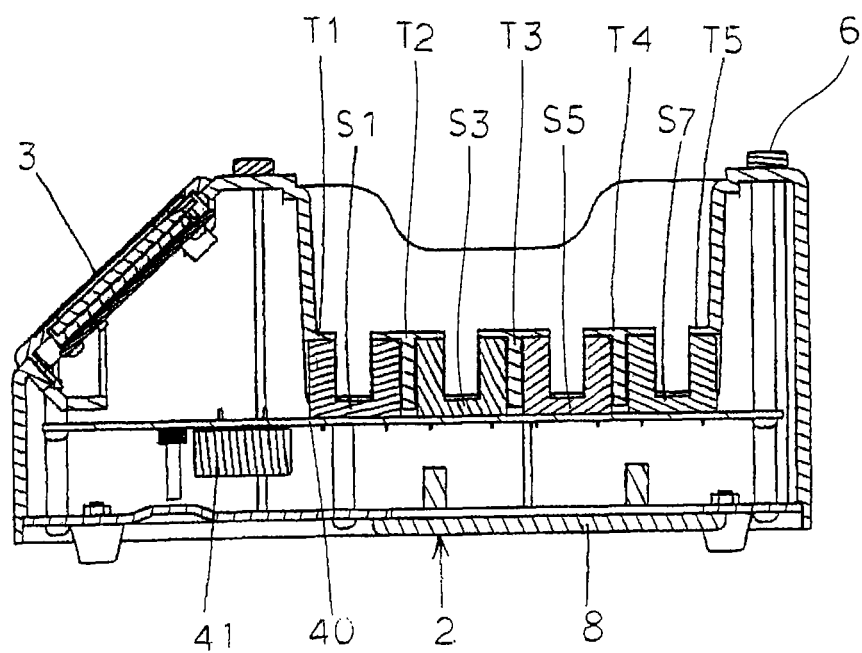
FIG. 22 is a cross-sectional view of the main body unit taken along line XXII-XXII in FIG. 20.
Figure 23:
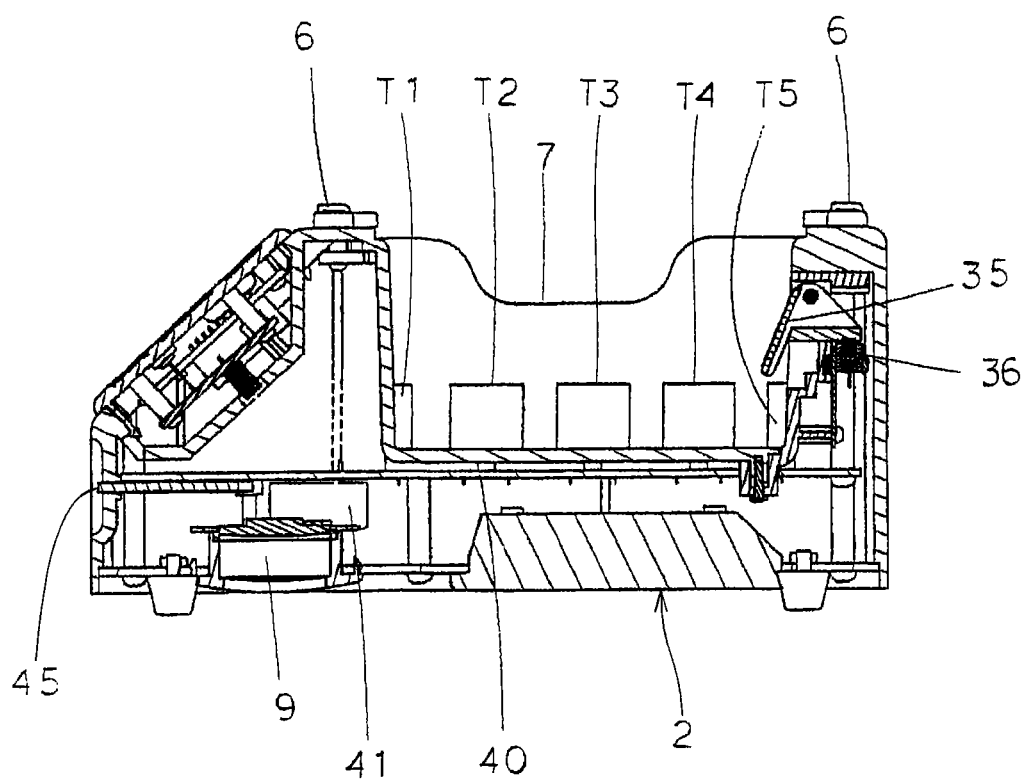
FIG. 23 is a cross-sectional view of the main body unit taken along line XXIII-XXIII in FIG. 20.

On the other hand, FIG. 18, FIG. 19 and FIG. 20 (a simplified view of FIG. 19) respectively show an external perspective view and a plan view (top view) of main body unit 2. FIG. 21 shows a cross-sectional view taken along line XXI-XXI in FIG. 20, FIG. 22 shows a cross-sectional view taken along line XXII-XXII in FIG. 20 and FIG. 23 shows a cross-sectional view taken along line XXIII-XXIII.

Main body unit 2 has a storage portion 30 for storing medicine package case 1. Nine projection portions T1-T9 are formed on the bottom of storage portion 30. Seven sensor portions S1-S7 are disposed as medicine package sensors at these projection portions T1-T9. Each of sensor portions S1-S7 uses a photocoupler including a light emitting diode L and a photodiode D. The distance between each of projection portions T1-T9, that is, the distance between the light emitting diode and the photodiode of the photocoupler being each of sensor portions S1-S7, is constant.

Projection portions T1-T5 are displaced from projection portions T6-T9 in said depth direction correspondingly to blocks 12(a-g) of medicine package case 1. In a state where medicine package case 1 is stored in storage portion 30 of main body unit 2, a medicine package rests on a bottom surface (bottom surface of blocks 12) of medicine package case 1 (see FIG. 24).

Figure 24:
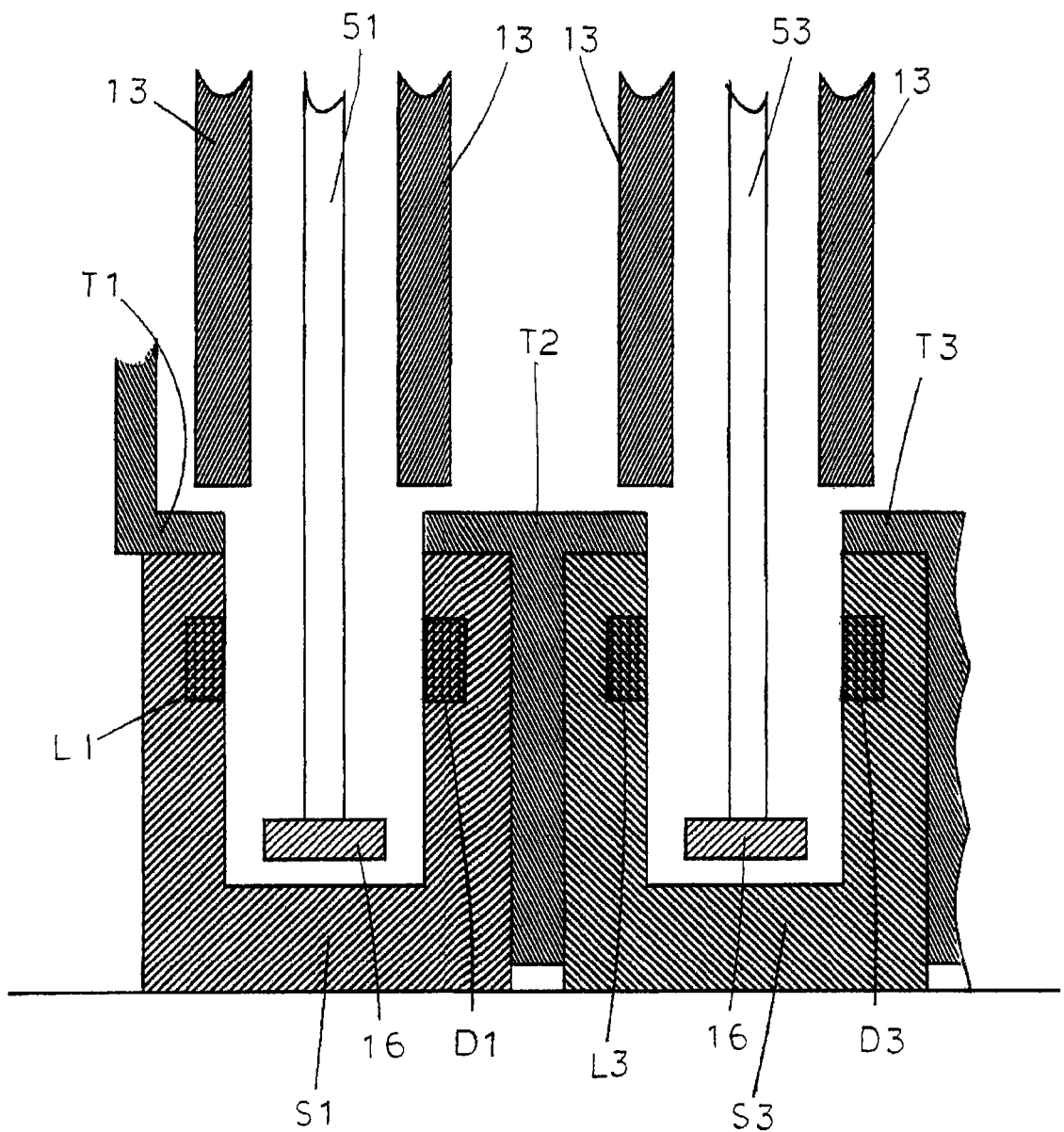
FIG. 24 is an enlarged cross-sectional view of a main part of the medication managing apparatus.

Though only partially shown in FIG. 24, only light-emitting diode L1 of sensor portion S1 is disposed at projection portion T1, photodiode D1 of sensor portion S1 and light-emitting diode L3 of sensor portion S3 are disposed at projection portion T2, photodiode D3 of sensor portion S3 and light-emitting diode L5 of sensor portion S5 are disposed at projection portion T3, photodiode D5 of sensor portion S5 and light-emitting diode L7 of sensor portion S7 are disposed at projection portion T4, and only photodiode D7 of sensor portion S7 is disposed at projection portion T5.

Furthermore, only light-emitting diode L2 of sensor portion S2 is disposed at projection portion T6, only photodiode D6 of sensor portion S6 is disposed at projection portion T9, photodiode D2 of sensor portion S2 and light-emitting diode L4 of sensor portion S4 are disposed at projection portion T7, and photodiode D4 of sensor portion S4 and light-emitting diode L6 of sensor portion S6 are disposed at projection portion T8. It is noted that the positions at which a light-emitting diode and a photodiode are disposed may be reversed.

In the case where medicine package case 1 is stored in storage portion 30, when no medicine package is present in blocks 12 of medicine package case 1, each paired light-emitting diodes and photodiodes (photocoupler) L1-D1, L2-D2, . . . , L7-D7 face each other through opening 15 of opposing wall 13 of block 12, and when a medicine package is present, each pair is blocked by the medicine package. In other words, when no medicine package is present in block 12, the photodiode receives light from the light-emitting diode, and when a medicine package is present, light is blocked by the medicine package and not received. A sense signal from L1-D1, L2-D2, . . . , L7-D7 is used to detect presence/absence of a medicine package in each block 12.

In addition, a switch lever 35 is swingably mounted on storage portion 30 in such a manner as to protrude from the wall surface in a normal state. A micro-switch 36 is provided in main body unit 2 which is turned on/off in a manner interlocked with switch lever 35 (FIG. 23). Here, switch lever 35 and micro-switch 36 constitute a medicine package case sensor.

In this medicine package sensor, when medicine package case 1 is not stored in storage portion 30, switch lever 35 protrudes from the wall surface of storage portion 30 to turn on micro-switch 36, and when medicine package case 1 is stored in storage portion 30, medicine package case 1 presses switch lever 35 to turn off micro-switch 36. Thus, the presence/absence of medicine package case 1 in storage portion 30 can be detected.

Alternatively, the on/off of micro-switch 36 may be reversed. More specifically, when medicine package case 1 is not stored in storage portion 30, micro-switch 36 may be turned off, and when stored, it may be turned on.

Though not shown in the figures, a cover opening/closing sensor for sensing opening/closing of cover 10 of medicine package case 1 is provided for main body unit 2. Based on a sense signal of this cover opening/closing sensor, it can readily be managed whether not only the user but also somebody else opens cover 10 of medicine package case 1.

Disposed inside main body unit 2 are light-emitting diodes L1-L7 and photodiodes D1-D7 of sensor portions S1-S7, micro-switch 36, and other electronic components 41, and in addition, a circuit board 40 to which display portion 3, button 4, speaker 9, a battery, and the like are electrically connected. A memory (not shown) in which medication-related information including the medication instruction time and the like are stored is installed on circuit board 40.

In the medication managing apparatus configured in this manner, when medicine package case 1 is stored in storage portion 30 of main body unit 2, medicine package case 1 presses switch lever 35 to turn off micro-switch 36 as described above, so that the presence of medicine package case 1 in storage portion 30 is detected. When medicine package case 1 is removed from storage portion 30, switch lever 35 returns to the original position and micro-switch 36 is turned on, so that the absence of medicine package case 1 in storage portion 30 is detected. On the other hand, when medicine package case 1 is stored in storage portion 30, flange 21 of medicine package case 1 positioned at flange reception portion 32 of main body unit 2 is fixed by slide knob 6 so that medicine package case 1 is not easily detached from storage portion 30.

On the other hand, as shown by an enlarged cross-sectional view of a main part in FIG. 24, when medicine package case 1 containing medicine packages 51-57 respectively in blocks 12(a-g) is stored in storage portion 30 of main body unit 2, blocks 12(a-g) of medicine package case 1 respectively correspond to sensor portions S1-S7 of main body unit 2 and medicine packages 51-57 and support piece 16 are positioned at respective gaps between sensor portions S1-S7. As a matter of course, as described above, each paired light-emitting diodes-photodiodes L1-D1, L2-D2, . . . , L7-D7 are opposed to each other through openings 15 of respective blocks 12(a-g).

In FIG. 24, as medicine package 51 is present in block 12a, light from light-emitting diode L1 of sensor portion S1 is blocked by medicine package 51 and photodiode D1 does not receive the light. Based on the sense signal from this L1-D1, the presence of medicine package 51 in block 12a is detected. The same applies to block 12c. By contrast, when medicine package 51 is not present in block 12a, photodiode D1 receives light from light-emitting diode L1, and the absence of a medicine package in block 12a is detected based on the sense signal from L1-D1.

According to this medication managing apparatus, medicine package case 1 containing medicine packages can be removed from main body unit 2, so that when medicines are handed to the user under an instruction of a doctor or the like, the user need only bring only medicine package case 1 removed from main body unit 2, and medicines can be given to/received from the user and the hospital (doctor) without causing much trouble to the user, as compared with the case where the user brings main body unit 2 including medicine package case 1. Moreover, it is not necessary to carry main body unit 2 including the management function portion such as the medicine package sensor (sensor portions S1-S7) and the medicine package case sensor (switch lever 35 and micro-switch 36), thereby ensuring a stable operation of main body unit 2 containing an electronic circuit and the like.

In addition, in medicine package case 1, blocks 12(a-g) are arranged in parallel with each other in the depth direction, each positioned orthogonally to the depth direction of main body unit 2, so that, in view of ergonomics, the medicine package stored in each of blocks 12 can easily be visually recognized, and a medicine package can easily be put into each block 12 and a medicine package can easily be taken out from each block 12.

Furthermore, since blocks 12(a-g) are arranged to be alternately displaced in the orthogonal direction, sensor portions S1-S7 occupy only small spaces of block 12, thereby reducing the size of not only medicine package case 1 but also the entire main body unit 2 including medicine package case 1, accordingly. Moreover, when blocks 12 are arranged alternately in the orthogonal direction, the positions of necessary medicine packages can be easily recognized thereby further facilitating removal of a medicine package.

In the foregoing embodiment, sensor portions S1-S7 as medicine package sensors are of a transmittance type in which a light-emitting diode and a photodiode are arranged opposed to each other. However, they may be of a reflectance type in which they are arranged on the same side. In this case, a medicine package may be light-reflective or light-absorptive depending on the manner of light detection. In the case of a light-reflective medicine package, in the presence of a medicine package, reflected light from the medicine package is received by the photodiode. In the case of a light-absorptive medicine package, in the absence of a medicine package, light from the light-emitting diode is reflected at the other side (opposing wall) and is then received by the photodiode.

In addition, if there is no particular need for individually specifying and monitoring medicine packages, a plurality of medicine packages may be detected by one sensor. For example, in the case where a transmittance-type sensor is used, it can be used in detection that the more medicine packages are, the less light passes through.

Figure 25:
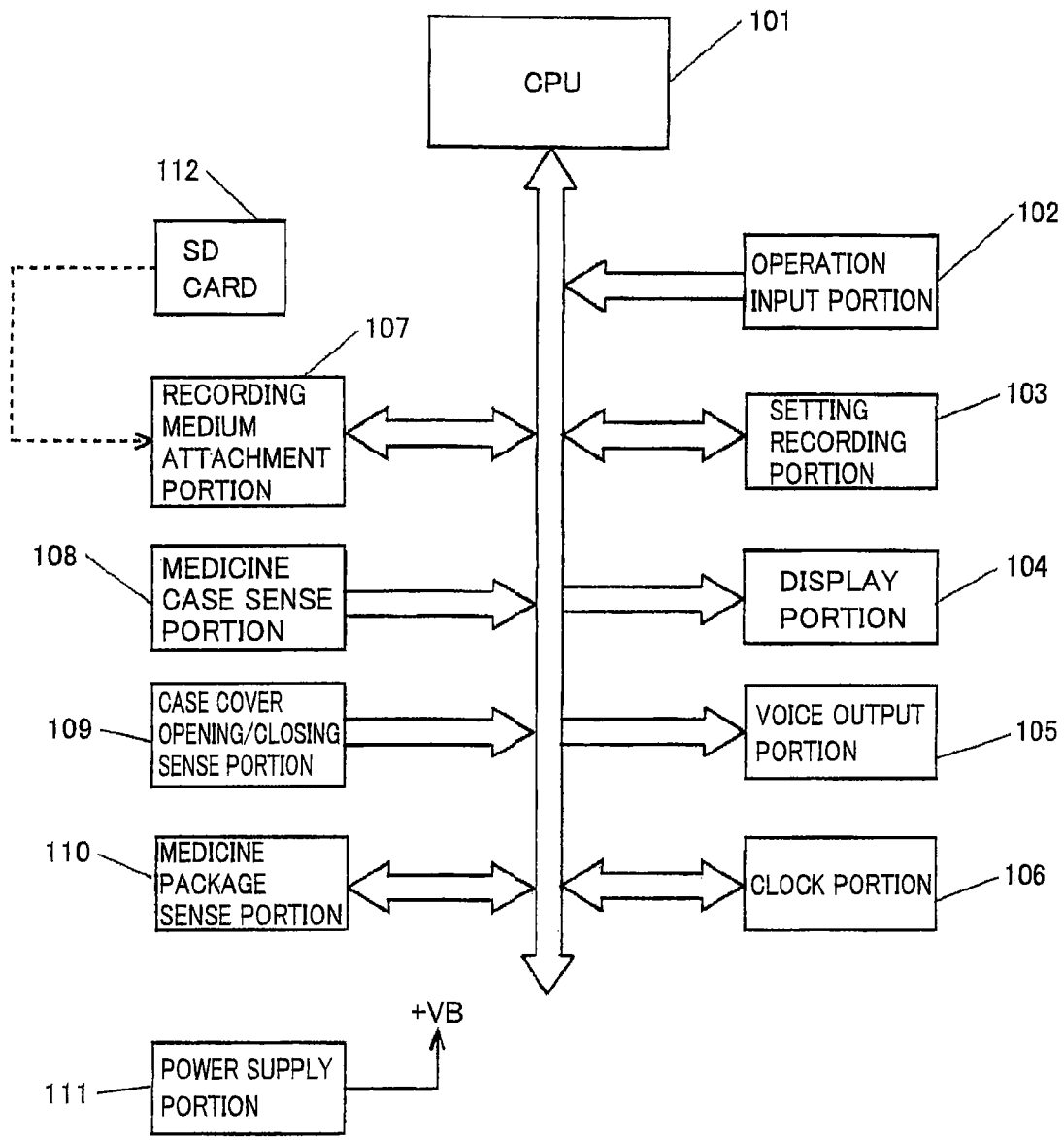
FIG. 25 is a block diagram showing a circuit configuration of the medication managing apparatus.
Figure 26:
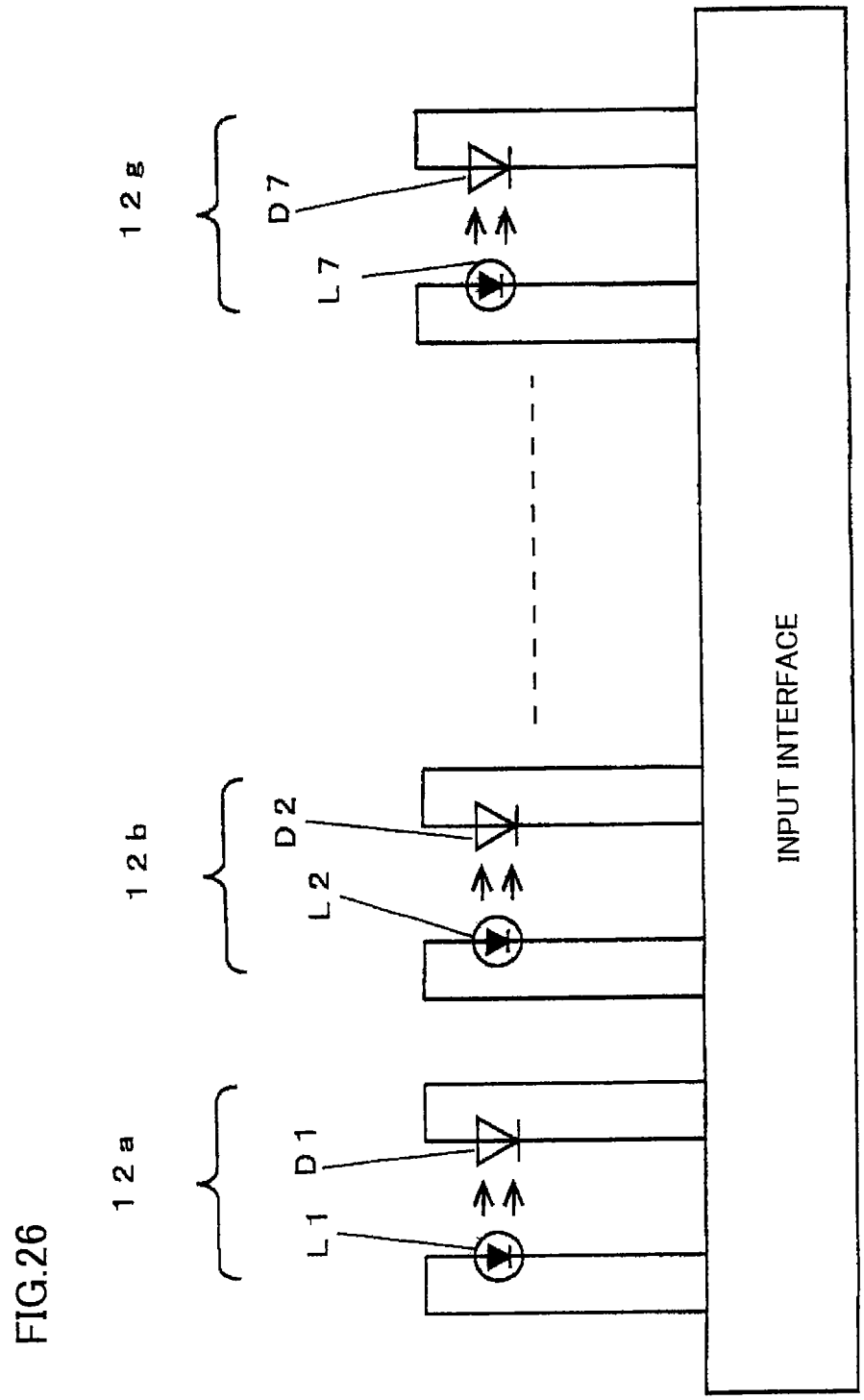
FIG. 26 is a diagram showing a schematic configuration of a medicine package sense portion in the block diagram of FIG. 25.
Figure 27:
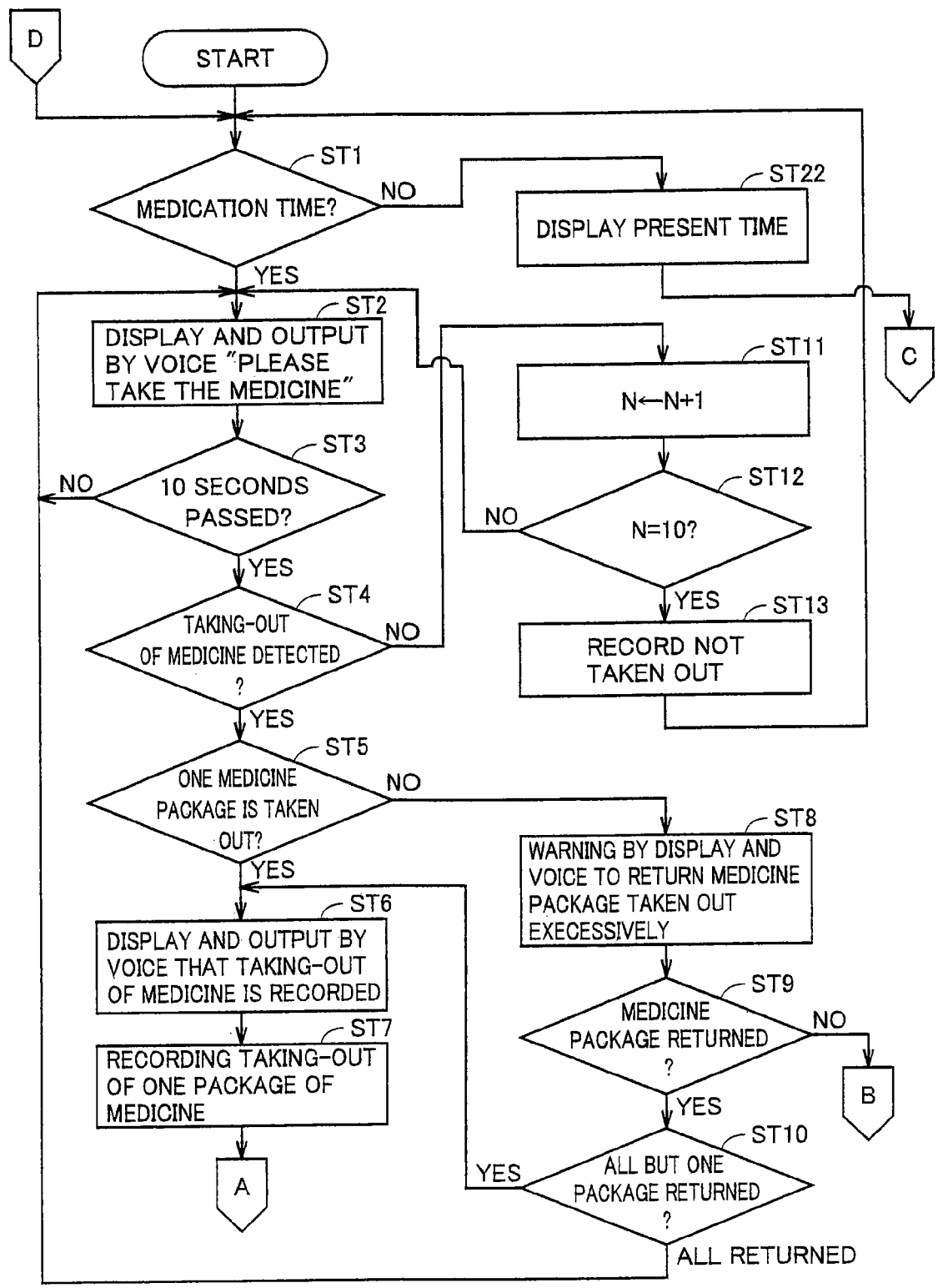
FIG. 27 is a flowchart illustrating a management processing operation of the medication managing apparatus.
Figure 28:
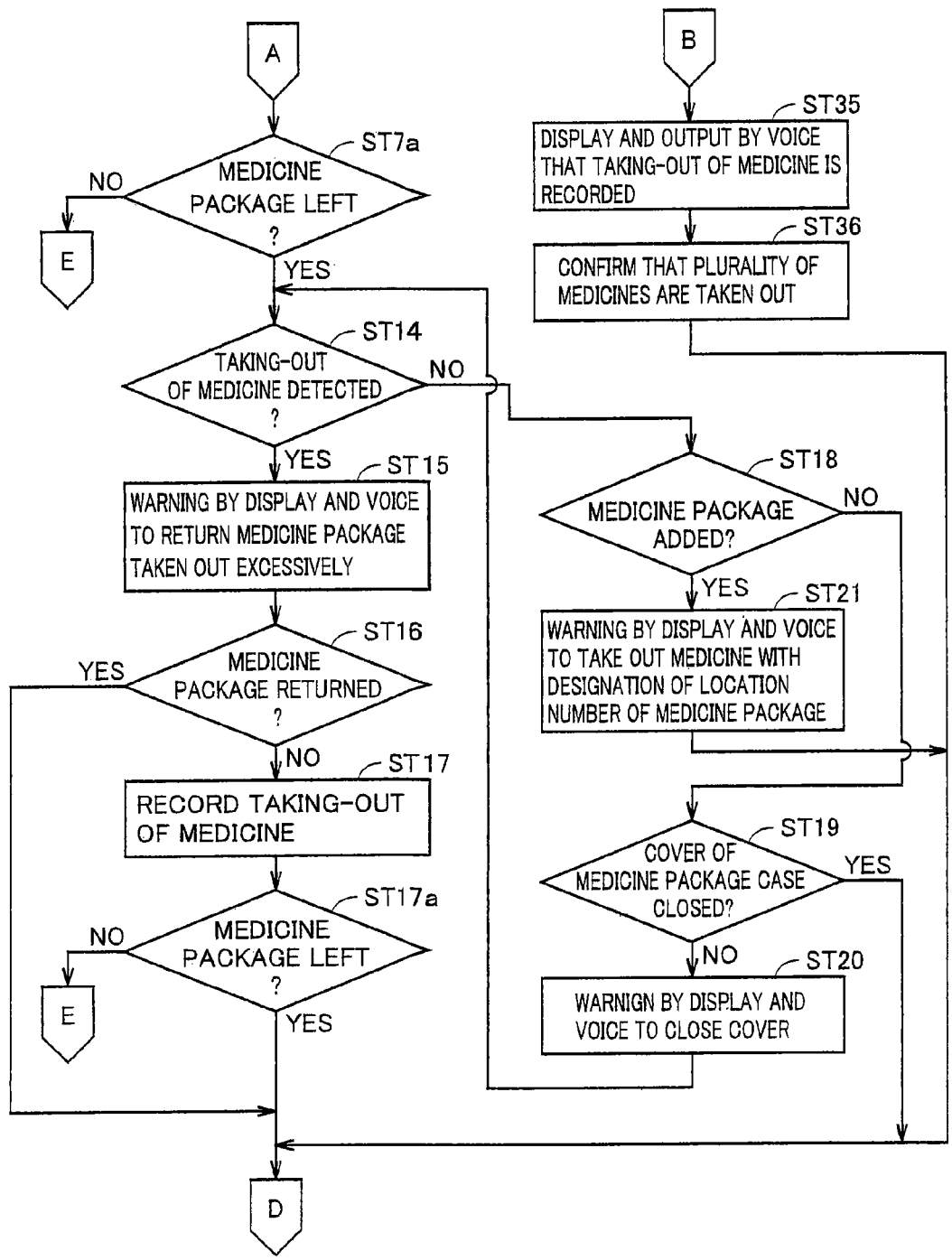
FIG. 28 is a flowchart illustrating the management processing operation of the medication managing apparatus, together with FIG. 27.
Figure 29:
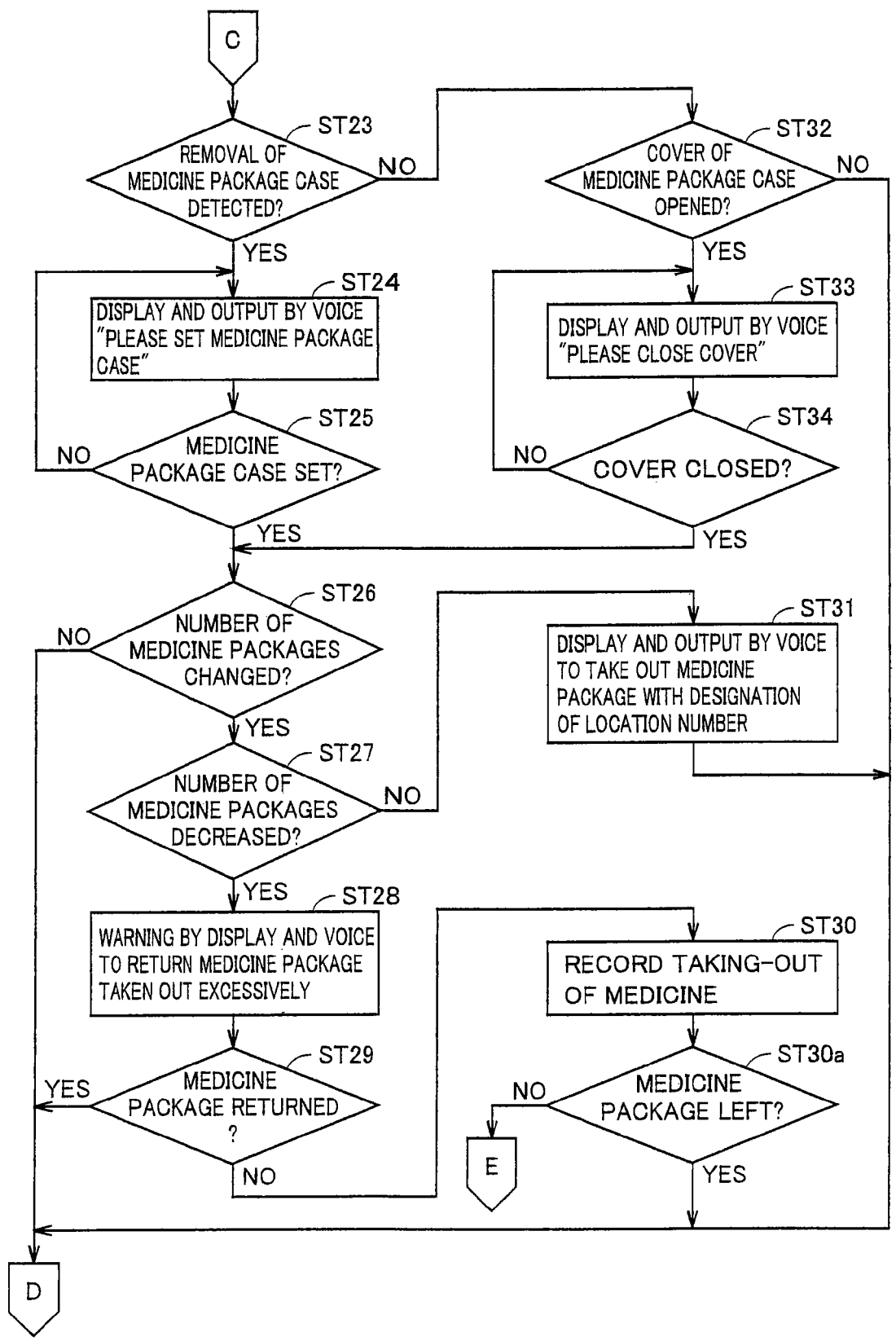
FIG. 29 is a flowchart illustrating the management processing operation of the medication managing apparatus, together with FIG. 27 and FIG. 28.

FIG. 25 is a block diagram showing a configuration of medication managing apparatus 100 of one embodiment of the present invention. This medication managing apparatus 100 includes a CPU 101 controlling the entire management processing, an operation input portion 102 including a power-supply switch, an up key, and a down key, a setting recording portion 103 recording the present time, a dosing notice time, and a variety of any other setting values, a display portion 104 (the aforementioned display portion 3) for displaying the present time, a dosing instruction, and any other instructions, a voice output portion 105 (the aforementioned speaker 9) outputting a dosing instruction, any other instructions and notices by voice, a clock portion 106 counting the time, a recording medium attachment portion 107 receiving the attached SD card 112 (the aforementioned SD card 45), a medicine package case sense portion 108 (the aforementioned switch lever 35 and micro-switch 36) sensing that medicine package case 1 is stored in main body unit 2, a case cover opening/closing sense portion 109 (the aforementioned cover opening/closing sensor) sensing opening/closing of cover 10 of medicine package case 1, a medicine package sense portion 110 (the aforementioned sensor portions S1-ST7) sensing the presence/absence of a medicine package in each medicine package storage portion of medicine package case 1, and a power supply portion 111 supplying a power supply voltage VB to each circuit component.

A dosing instruction time and a main body unit ID are stored in SD card 112 when medicines are provided from a doctor to a recipient of drugs. SD card 112 additionally includes a region for storing the actual dosing time and any other management information. As shown in FIG. 16, medicine package sense portion 110 is provided with a photocoupler formed of light-emitting diode L1 and photodiode D1 in each medicine package storage portion.

The medication managing apparatus of the present invention manages whether or not the present time is the scheduled medication time. It executes separate processes when the medication time has not come and when the medication time has come.

Transiting from a medication waiting state, when the medication time has come, firstly a notice is given by display and voice that the medication time has come, Next, in a prescribed time period, it is determined whether or not any medicine packages are taken out from medicine package case 1. If they are taken out, then it is determined how many medicine packages are taken out. If no medicine packages are taken out because the recipient is not aware of the medication time or does not take the medicine, the notice that the medication time has come is given repeatedly for ten times at ten-second intervals. If the medicine package is still not taken out, it is stored in SD card 112 that the medicine package is not taken out.

If a plurality of medicine packages are taken out, a warning/notice is given to return the medicine packages taken out excessively. In response to the warning/notice, if all the medicine packages taken out are returned, then again a notice that the medication time has come is given. If the taken out medicine packages are not returned, a notice that the taking-out of the medicine packages is recorded is given, and the number of the taken out medicine packages is stored in SD card 112. Further, if all the taken out medicine packages but one are returned, then the process is executed similarly to the case where firstly one medicine package is taken out when a notice that the medication time has come is given.

In the case where firstly one medicine package is taken out when a notice that the medication time has come is given, a notice of medication acknowledgement is given ten seconds after the medicine package is taken out. On the other hand, if a further medicine package is taken out, a warning/notice is given to return the excessively taken out medicine package. If no medicine package is returned in response to the warning, then it is assumed that the medicine package is taken out, and it is recorded in SD card 112.

In the case where firstly one medicine package is taken out, the notice of medication acknowledgement is given ten seconds after the medicine package is taken out. If cover 10 of medicine package case 1 is not closed after the notice, a warning is given to close the same. If a further medicine package is taken out thereafter, a warning/notice to return the excessively taken out medicine package is given. If no medicine package is returned in response to the warning, it is assumed that the medicine package is taken out, and it is recorded in SD card 112.

In the case where firstly one medicine package is taken out when the notice that the medication time has come is given, and the notice of medication acknowledgement is given ten seconds after the medicine package is taken out, if thereafter any medicine package is added disorderly, then a warning is given to take out the medicine package, with designation of a location number of the medicine package.

In the waiting state at the time except for the medication time, whether or not medicine package case 1 is taken out and whether or not cover 10 of medicine package case 1 is opened are managed. If medicine package case 1 is taken out, then a warning to return the medicine package is given. Thereafter, when medicine package case 1 is returned, it is determined whether or not the number of the medicine packages is changed. If the number is not changed, it goes back to the waiting screen. If the number decreases, then a warning is given to return the excessively taken out medicine package. If the medicine package is not returned while the warning is given, then it is assumed that the medicine package is taken out, and it is recorded in SD card 112. If the number increases, then an instruction/notice is given to take out the medicine package, with designation of a location number of the medicine package.

If cover 10 of medicine package 1 is opened, then an instruction/notice is given to close the cover. If cover 10 of medicine package 1 is closed thereafter, then it is determined whether or not the number of medicine packages is changed. If the number is not changed, then it returns to the waiting screen. If the number decreases, then a warning is given to return the excessively taken out medicine packages. If the medicine package is not returned while the warning is given, then it is assumed that the medicine package is taken out, and it is recorded in SD card 112. If the number increases, then an instruction/notice is given to take out the medicine package, with designation of a location number of the medicine package.

Next, referring to the flowcharts shown in FIG. 27-FIG. 30, the managing processing operation of this medication managing apparatus will be described. Upon the start of the process, first, at step ST1, it is determined whether or not the medication time has come. If the medication time has not come, the process proceeds to step ST22. On the other hand, if the medication time has come, the process proceeds to step ST2. In the process in steps ST2-ST20, the management at the time when the medication time has come is executed.

At step ST2, "Please take one package of medicine" appears on display portion 104, and "It is time to take your medicine. Please take out one package of medicine" is output by voice from voice output portion 105. Then, the process proceeds to step ST3. At step ST3, the process waits for ten seconds to pass and then proceeds to step ST4.

At step ST4, it is determined whether or not taking out of medicine is detected. If it is detected at medicine package sense portion 110 that the recipient takes out the medicine, the process proceeds to step ST5. On the other hand, if the medicine is not taken out, the process proceeds to step ST1. At step ST11, a variable N is incremented by one (initially, N=0), and the process then proceeds to step ST12. At step ST12, whether N=10 or not is determined. As initially N=1, if determination is "NO", the process returns to step ST2. At step ST2, again, "Please take the medicine" is displayed and output by voice. Then, if the medicine is not taken out after the notice "please take the medicine" at the medication time, the notice "please take the medicine" is repeated every ten seconds. If the medicine is not taken out even after the notice is repeated ten times, the determination at step ST12 is "YES", and the process proceeds to step ST13. At step ST13, it is stored in SD card 112 that the medicine is not taken out at this medication instruction time. Then, the process returns to step ST2.

At step ST5, it is determined whether or not one medicine package is taken out. If one package is taken out, the process proceeds to step ST6. On the other hand, if a plurality of packages, rather than one, are taken out, the process proceeds to step ST8. At step ST6, it is displayed and output by voice that the taking out of the medicine is recorded, at display portion 104 and voice output portion 105. Then, the process proceeds to step ST7. At step ST7, the taking-out of one medicine package is recorded together with the taking-out time in SD card 112. Then, the process proceeds to step ST7*a*. At step ST7*a*, it is determined whether or not a medicine package is left. If left, the process proceeds to step ST14. On the other hand, if not left, the process proceeds to step ST37.

At step ST8, it is displayed and warned by voice to return the medicine package taken out excessively. Then, the process proceeds to step ST9. At step ST9, it is determined whether or not the medicine package has been returned. If the medicine package has been returned, the process proceeds to step ST10. On the other hand, if the medicine package is not returned, the process proceeds to step ST35. At step ST35, it is displayed and output by voice that "Taking-out of two or more medicines will be recorded". Then, the process proceeds to step ST36. At step ST36, it is recorded in SD card 112 that a plurality of medicine packages are taken out. Then, the process returns to step ST1.

At step ST10, it is determine whether all but one medicine package is returned or all are returned. If all but one is returned, the process proceeds to step ST6. Then, at step ST6, it is displayed and output by voice that the taking-out of medicine is recorded, and then at step ST7, the taking-out of one medicine package is recorded in SD card 112. Then, the process proceeds to step ST14. On the other hand, if at step ST10, all of the medicine packages taken out are returned, the process returns to step ST2.

At step ST14, it is further determined whether or not taking-out of medicine is detected. If taking-out of medicine is detected, the process proceeds to step ST15. On the other hand, if taking-out of medicine is not detected, the process proceeds to step ST18. At step ST15, a warning is displayed at display portion 104 and output by voice from voice output portion 105 to return the medicine package taken out excessively. Then, the process proceeds to step ST16. At step ST16, it is determined whether or not the medicine package has been returned. If the medicine package has been returned, the process returns to step ST1. On the other hand, if not returned, it is assumed that the medicine that has not been returned was taken out, and the process then proceeds to step ST17 to record taking-out of medicine in SD card 112. Then, the process proceeds to step ST17*a*. At step ST17*a*, it is determined whether or not a medicine package is left. If left, the process returns to step ST1. On the other hand, if not left, the process proceeds to step ST37.

At step ST18, it is determined whether or not a medicine package is added. If a medicine package is added to medicine package case 1, for example, by returning one of the medicines taken out which should not be returned, the process proceeds to step ST21. On the other hand, if a medicine package is not added, the process proceeds to step ST19. At step ST21, a warning is displayed at display portion 104 and output by voice from voice output portion 105 to take out a medicine package with designation of a location number of the medicine package. Then, the process returns to step ST1.

At step ST19, it is determined whether or not cover 10 of medicine package case 1 has been closed. If cover 10 has been closed, the process returns to step ST 1. On the other hand, if the cover is not closed, the process proceeds to step ST20. At step ST20, a warning is displayed at display portion 104 and output by voice from voice output portion 105 to close the cover. Then, the process returns to step ST14.

Next, the process at the time other than the medication time will be described. At step ST1, if it is determined that the present time is not the medication time, the process proceeds to step ST22 and the present time appears on display portion 104. Then, the process proceeds to step ST23. At step ST23, it is determined whether or not the medicine package case is removed. If medicine package case 1 is not removed from main body unit 2, the process proceeds to step ST32. On the other hand, if it is detected that medicine package case 1 is removed from main body unit 2, the process proceeds to step ST24.

At step ST32, it is determined whether or not the cover of the medicine package case is opened. If the cover is not opened, the step returns to step ST1. On the other hand, if the cover is opened, the process proceeds to step ST33. At step ST33, "please close the cover" is displayed at display portion 104 and output by voice from voice output portion 105. Then, the process proceeds to step ST34. At step ST34, it is determined whether or not the cover is closed. If not closed, the process returns to step ST33. On the other hand, if the cover is closed, the process proceeds to step ST26.

At step ST24, as medicine package case 1 is removed, "please set the medicine package case" is displayed at display portion 104 and output by voice from voice output portion 105. Then, the process proceeds to step ST25. At step ST25, it is determined whether or not medicine package case 1 is set. If medicine package case 1 is not set, the process returns to step ST24. On the other hand, if medicine package case 1 is set, the process proceeds to step ST26.

At step ST26, it is determined whether or not the number of medicine packages changes. If the number of medicine packages is not changed, the process returns to step ST1. On the other hand, if the number of medicine packages is changed, the process proceeds to step ST27. At step ST27, it is determined whether or not the number of medicine packages decreases. If the number of medicine packages decreases, the process proceeds to step ST28. On the other hand, if the number of medicine packages does not decrease (if increase), the process proceeds to step ST31.

At step ST28, a warning is displayed at display portion 104 and output by voice from voice output portion 105 to return the medicine package taken out excessively. Then, the process proceeds to step ST29. At step ST29, it is determined whether or not the medicine package has been returned. If returned, the process returns to step ST 1. On the other hand, if the medicine package is not returned, the process proceeds to step ST30.

At step ST30, that a medicine package is taken out is recorded together with the time in SD card 112. Then, the process proceeds to step ST30*a*. At step ST30*a*, it is determined whether or not a medicine package is left. If left, the process returns to step ST1. On the other hand, if not left, the process proceeds to step ST37.

At step ST31, it is displayed at display portion 104 and output by voice from voice output portion 105 to take out a medicine package with designation of the location number thereof. Then, the process returns to step ST1.

At step ST37, such a guidance that "please set the next case" is given by display and voice to replace the medicine package case. Then, the process proceeds to step ST38. At step ST38, it is determined whether or not the medicine package case has been replaced. If the replacement is confirmed, the process returns to step ST1. On the other hand, if not yet replaced, the process returns to step ST37 and a guidance is given again by display and voice to replace the medicine package case.

INDUSTRIAL APPLICABILITY

According to the present invention, that a medicine is taken out is recorded in the case where the stored medication time has come and in the case of the other times. In each case, various changes other than the taking-out are stored. Therefore, detailed medication management can be achieved, and detailed data as to medication can be sold.

The invention claimed is:
1. A medication managing apparatus, comprising:
a medicine package storage portion comprising a plurality of blocks each storing a medicine package containing a single dose of medicine for a user;
storing device storing in advance a plurality of medication times;
medication time noticing device giving a notice, every time the medication time has come, that the medication time has come;
a medicine package sensor sensing presence/absence of the medicine package in the block of the medicine package storage portion;
a processing device configured to, when the medication time has come, determine by the medicine package sensor presence/absence of the medicine package in a prescribed block, to cause the storing device to store a time point of the determination and the presence/absence of the medicine package, and to output an instruction for the user in accordance with a detection result, the processing device being further configured to, when taking-out of the medicine package is sensed by the medicine package sensor at a time except for the medication time, cause the storing device to store a time point of the sensing and the taking-out, and to output a desired instruction to the user,
wherein the medicine package storage portion comprising a medicine package case removably attached to a main body of the medication package storage portion,
the medication managing apparatus comprises a medicine package case sensor sensing attachment and removal of the medicine package case to and from the main body,
the processing device gives an instruction/notice to set the medicine package case if taking-out of the medicine package case is sensed at a time except for the medication time, and
the processing device is configured to determine whether or not the medicine package case is set, detects whether there is a change in number of the medicine packages when the medicine package case is set, and gives an instruction/notice to take out the medicine package with designation of location of the medicine package if the number of the medicine packages increases.
2. The medication managing apparatus according to claim 1 wherein the storing device is a storage medium externally attached to a main body of the medication managing appara- tus, and the medication managing apparatus comprises a storage medium attachment portion for attaching the storage medium.

3. The medication managing apparatus according to claim 1, further comprising a function of comparing an identification key of the medication managing apparatus and an identification key of the storage medium in order to attain one-on-one recognition of the medication managing apparatus and the storage medium.

4. The medication managing apparatus according to claim 1, wherein the medication time or information being necessary to be set individually for each user, including display/guidance information, is stored in advance in the storing medium so that it can be reflected on a main body of the medication managing apparatus.

5. The medication managing apparatus according to claim 1, wherein the medication managing apparatus gives an instruction/notice to add a medicine package or replace the medicine package case with a new medicine package case if remaining quantity of the medicine package in the medicine package case reaches zero.

6. The medication managing apparatus according to claim 1, wherein the processing device is configured to determine whether or not the medicine package case is set, detects whether there is a change in number of the medicine packages when the medicine package case is set, and gives a notice to return part of medicine packages that is taken out in excess of one if the number of the medicine packages decreases.

7. The medication managing apparatus according to claim 6, wherein the processing device is configured to determine whether or not the medicine package is returned based on an output of the medicine package sensor, and if it is not returned, the processing device stores in the storing device taking-out of the medicine package together with a time point.

8. A medication managing apparatus, comprising:
a medicine package storage portion comprising a plurality of blocks each storing a medicine package containing a single dose of medicine for a user;
storing device storing in advance a plurality of medication times;
medication time noticing device giving a notice, every time the medication time has come, that the medication time has come;
a medicine package sensor sensing presence/absence of the medicine package in the block of the medicine package storage portion;
a processing device configured to, when the medication time has come, determine by the medicine package sensor presence/absence of the medicine package in a prescribed block, to cause the storing device to store a time point of the determination and the presence/absence of the medicine package, and to output an instruction for the user in accordance with a detection result, the processing device being further configured to, when taking-out of the medicine package is sensed by the medicine package sensor at a time except for the medication time, cause the storing device to store a time point of the sensing and the taking-out, and to output a desired instruction to the user,
wherein the medicine package storage portion is provided with an openable/closable cover covering the entire blocks,
the medication managing apparatus comprises a cover opening/closing sensor sensing opening/closing of the cover,
the processing device gives an instruction/notice to close the cover when the cover is opened at a time except for the medication time, and
the processing device is configured to determine whether or not the cover is closed, detects whether there is a change in number of the medicine packages when the cover is closed, and gives an instruction/notice to take out the medicine package with designation of location of the medicine package if the number of the medicine packages increases.

9. The medication managing apparatus according to claim 8, wherein the processing device is configured to determine whether or not the cover is closed, detects whether there is a change in number of the medicine packages when the cover is closed, and gives a notice to return part of medicine packages that is taken out in excess of one if the number of the medicine packages decreases.

10. The medication managing apparatus according to claim 8 wherein the medicine package storage portion is constituted of a medicine package case removably attached to a main body, and the medication managing apparatus gives an instruction/notice to add a medicine package or replace the medicine package case with a new medicine package case if remaining quantity of the medicine package in the medicine package case reaches zero.

11. The medication managing apparatus according to claim 8 wherein the storing device is a storage medium externally attached to a main body of the medication managing apparatus, and the medication managing apparatus comprises a storage medium attachment portion for attaching the storage medium.

12. The medication managing apparatus according to claim 8, further comprising a function of comparing an identification key of the medication managing apparatus and an identification key of the storage medium in order to attain one-on-one recognition of the medication managing apparatus and the storage medium.

13. The medication managing apparatus according to claim 8, wherein the medication time or information being necessary to be set individually for each user, including display/guidance information, is stored in advance in the storing medium so that it can be reflected on a main body of the medication managing apparatus.

* * * * *